(12) United States Patent
Doan et al.

(10) Patent No.: US 10,456,583 B2
(45) Date of Patent: Oct. 29, 2019

(54) CUSTOMIZED PRIMING BY NEUROMODULATION DEVICE

(71) Applicant: Boston Scientific Neuromodulation Corporation, Valencia, CA (US)

(72) Inventors: Que T. Doan, West Hills, CA (US); Bradley Lawrence Hershey, Valencia, CA (US); Changfang Zhu, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 60 days.

(21) Appl. No.: 15/611,068

(22) Filed: Jun. 1, 2017

(65) Prior Publication Data

US 2017/0348535 A1 Dec. 7, 2017

Related U.S. Application Data

(60) Provisional application No. 62/344,905, filed on Jun. 2, 2016.

(51) Int. Cl.
*A61N 1/372* (2006.01)
*A61N 1/36* (2006.01)
*A61N 1/05* (2006.01)
*A61N 1/08* (2006.01)

(52) U.S. Cl.
CPC ..... *A61N 1/37241* (2013.01); *A61N 1/36057* (2013.01); *A61N 1/36071* (2013.01); *A61N 1/36125* (2013.01); *A61N 1/36139* (2013.01); *A61N 1/36164* (2013.01); *A61N 1/0551* (2013.01); *A61N 2001/083* (2013.01)

(58) Field of Classification Search
USPC .......................................................... 607/46
See application file for complete search history.

(56) References Cited

U.S. PATENT DOCUMENTS

| 5,292,340 A | 3/1994 | Crosby et al. |
|---|---|---|
| 5,775,331 A | 7/1998 | Raymond et al. |
| 8,412,345 B2 | 4/2013 | Moffitt |

(Continued)

FOREIGN PATENT DOCUMENTS

| WO | WO-9639932 A1 | 12/1996 |
|---|---|---|
| WO | WO-2016154091 A1 | 9/2016 |

(Continued)

OTHER PUBLICATIONS

"International Application Serial No. PCT/US2016/029735, International Search Report dated Jul. 12, 2016", 3 pgs.

(Continued)

*Primary Examiner* — Carl H Layno
*Assistant Examiner* — Erin M Piateski
(74) *Attorney, Agent, or Firm* — Schwegman Lundberg & Woessner, P.A.

(57) ABSTRACT

A neuromodulation device is configured with a set of testing program configuration instructions including therapeutic neuromodulation field-setting parameters. The device determines a custom priming program in response to the testing program configuration instructions. The custom priming program controls the neuromodulation device to generate a priming field with specific correspondence to the therapeutic neuromodulation field to be produced by the testing program.

20 Claims, 18 Drawing Sheets

(56) References Cited

U.S. PATENT DOCUMENTS

| | | | |
|---|---|---|---|
| 10,226,627 | B2 | 3/2019 | Doan et al. |
| 2009/0005845 | A1 | 1/2009 | David et al. |
| 2011/0054564 | A1* | 3/2011 | Valencia ............ A61N 1/36021 607/46 |
| 2011/0184486 | A1 | 7/2011 | De Ridder |
| 2013/0204315 | A1 | 8/2013 | Wongsarnpigoon et al. |
| 2013/0282078 | A1 | 10/2013 | Wacnik |
| 2014/0277267 | A1* | 9/2014 | Vansickle .......... A61N 1/36071 607/46 |
| 2015/0032181 | A1* | 1/2015 | Baynham ............ A61N 1/3615 607/46 |
| 2015/0165202 | A1 | 6/2015 | Grandhe |
| 2016/0082262 | A1 | 3/2016 | Parramon et al. |
| 2016/0271413 | A1* | 9/2016 | Vallejo ................... A61N 2/008 |
| 2016/0317815 | A1 | 11/2016 | Doan |
| 2017/0348530 | A1 | 12/2017 | Doan et al. |
| 2017/0348540 | A1 | 12/2017 | Doan et al. |

FOREIGN PATENT DOCUMENTS

| | | |
|---|---|---|
| WO | WO-2016176425 A1 | 11/2016 |
| WO | WO-2017210382 A1 | 12/2017 |
| WO | WO-2017210401 A1 | 12/2017 |
| WO | WO-2017210433 A1 | 12/2017 |

OTHER PUBLICATIONS

"International Application Serial No. PCT/US2016/029735, Written Opinion dated Jul. 12, 2016", 4 pgs.
"U.S. Appl. No. 15/141,075, Corrected Notice of Allowability dated Dec. 11, 2018", 5 pgs.
"U.S. Appl. No. 15/141,075, Examiner Interview Summary dated Oct. 11, 2018", 3 pgs.
"U.S. Appl. No. 15/141,075, Final Office Action dated Aug. 9, 2018", 11 pgs.
"U.S. Appl. No. 15/141,075, Non Final Office Action dated Jan. 12, 2018", 10 pgs.
"U.S. Appl. No. 15/141,075, Notice of Allowance dated Oct. 25, 2018", 7 pgs.
"U.S. Appl. No. 15/141,075, Response filed Apr. 12, 2018 to Non Final Office Action dated Jan. 12, 2018", 10 pgs.
"U.S. Appl. No. 15/141,075, Response filed Oct. 8, 2018 to Final Office Action dated Aug. 9, 2018", 11 pgs.
"U.S. Appl. No. 15/610,839, Examiner Interview Summary dated Nov. 26, 2018", 3 pgs.
"U.S. Appl. No. 15/610,839, Final Office Action dated Oct. 25, 2018", 16 pgs.
"U.S. Appl. No. 15/610,839, Non Final Office Action dated Jun. 29, 2018", 18 pgs.
"U.S. Appl. No. 15/610,839, Notice of Allowance dated Jan. 17, 2019", 7 pgs.
"U.S. Appl. No. 15/610,839, Response filed Oct. 1, 2018 to Non Final Office Action dated Jun. 29, 2018", 12 pgs.
"U.S. Appl. No. 15/610,839, Response filed Dec. 10, 2018 to Final Office Action dated Oct. 25, 2018", 11 pgs.
"U.S. Appl. No. 15/611,473, Non Final Office Action dated Jan. 14, 2019", 8 pgs.
"European Application Serial No. 16720690.3, Response filed Aug. 3, 2018 to Communication Pursuant to Rules 161(2) and 162 EPC dated Feb. 7, 2018", 12 pgs.
"International Application Serial No. PCT/US2016/029735, International Preliminary Report on Patentability dated Nov. 9, 2017", 6 pgs.
"International Application Serial No. PCT/US2017/035365, International Preliminary Report on Patentability dated Dec. 13, 2018", 8 pgs.
"International Application Serial No. PCT/US2017/035365, International Search Report dated Sep. 6, 2017", 5 pgs.
"International Application Serial No. PCT/US2017/035365, Written Opinion dated Sep. 6, 2017", 6 pgs.
"International Application Serial No. PCT/US2017/035401, International Preliminary Report on Patentability dated Dec. 13, 2018", 9 pgs.
"International Application Serial No. PCT/US2017/035401, International Search Report dated Aug. 10, 2017", 8 pgs.
"International Application Serial No. PCT/US2017/035401, Written Opinion dated Aug. 10, 2017", 9 pgs.
"International Application Serial No. PCT/US2017/035460, International Preliminary Report on Patentability dated Dec. 13, 2018", 8 pgs.
"International Application Serial No. PCT/US2017/035460, International Search Report dated Sep. 8, 2017", 5 pgs.
"International Application Serial No. PCT/US2017/035460, Written Opinion dated Sep. 8, 2017", 8 pgs.

* cited by examiner

CUSTOMIZED PRIMING BY NEUROMODULATION DEVICE

CLAIM OF PRIORITY

This application claims the benefit of priority under 35 U.S.C. § 119(e) of U.S. Provisional Patent Application Ser. No. 62/344,905, filed on Jun. 2, 2016, which is herein incorporated by reference in its entirety.

TECHNICAL FIELD

This document relates generally to medical devices, and more particularly, to systems, devices and methods for delivering neuromodulation.

BACKGROUND

Neuromodulation (or "neural neuromodulation", also referred to as "neurostimulation" or "neural stimulation") has been proposed as a therapy for a number of conditions. Often, neuromodulation and neural stimulation may be used interchangeably to describe excitatory stimulation that causes action potentials as well as inhibitory and other effects. Examples of neuromodulation include Spinal Cord Stimulation (SCS), Deep Brain Stimulation (DBS), Peripheral Nerve Stimulation (PNS), and Functional Electrical Stimulation (FES). SCS, by way of example and not limitation, has been used to treat chronic pain syndromes.

Conventional SCS delivers electrical pulses to the spinal cord, masking the transmission of pain signals to the brain. While these electrical pulses can reduce pain, they are often associated with possible unpleasant tingling and buzzing sensations known as paresthesia.

Sub-perception SCS therapy has been proposed to provide pain relief without the accompanying paresthesia. However, the wash-in time for sub-perception SCS therapy is significant. The wash-in time refers to a time from the start of a therapy to when a therapeutic response to the therapy can be observed. Since there typically is no immediate feedback for a sub-perception SCS, it can be a challenge to find a desirable or optimal location (sweet-spot) for the neuromodulation field within an office visit.

SUMMARY

The following examples illustrate various aspects of the embodiments described herein.

Example 1 is directed to an apparatus for a neuromodulation system, comprising: neuromodulation generator circuitry configured to use electrodes of an electrode arrangement to generate neuromodulation fields including: a therapeutic neuromodulation field to produce a therapeutic effect in therapy-targeted neural tissue; and a priming field to produce a priming effect in priming-targeted neural tissue, wherein the priming effect causes a change in sensitization of the priming-targeted neural tissue to the therapeutic neuromodulation field; and a controller configured to receive testing program configuration instructions including therapeutic neuromodulation field-setting parameters, wherein the controller is further configured to determine a custom priming program in response to the testing program configuration instructions, wherein the custom priming program controls the neuromodulation generator circuitry to generate the priming field with specific correspondence to the therapeutic neuromodulation field to be produced by the testing program.

In Example 2, the subject matter of Example 1 optionally includes wherein the controller is to initiate the custom priming program prior to execution of the testing program.

In Example 3, the subject matter of any one or more of Examples 1-2 optionally include wherein the therapeutic neuromodulation field-setting parameters define a plurality of therapeutic neuromodulation field locations in the therapy-targeted neural tissue, and wherein the custom priming program is adapted to cause the neuromodulation generator circuitry to produce at least one priming field having specific spatial correspondence to the plurality of therapeutic neuromodulation field locations.

In Example 4, the subject matter of any one or more of Examples 1-3 optionally include wherein the controller is further configured to adapt the custom priming program in response to a result of execution of the testing program to focus the custom priming program on a selected set of the therapeutic neuromodulation field-setting parameters determined to be most effective by execution of the testing program.

In Example 5, the subject matter of any one or more of Examples 1-4 optionally include wherein the custom priming program is determined by local processing operations performed by the controller by application of predefined decision criteria stored locally on the apparatus and accessible by the controller.

In Example 6, the subject matter of any one or more of Examples 1-5 optionally include wherein the custom priming program is determined by the controller, wherein the controller is to receive the custom priming program from a remote device.

In Example 7, the subject matter of any one or more of Examples 1-6 optionally include wherein the controller is configured to execute the custom priming program to generate the priming field during execution of the testing program.

In Example 8, the subject matter of Example 7 optionally includes wherein the testing program defines a plurality of distinct therapeutic neuromodulation field locations in the therapy-targeted neural tissue to be targeted at corresponding different times, including a first location and a second location; and wherein the custom priming program is to cause the neuromodulation generator circuitry to direct the priming field to the second location during application of the therapeutic neuromodulation field to the first location.

In Example 9, the subject matter of any one or more of Examples 7-8 optionally include wherein the controller is configured to determine the custom priming program based on the testing program such that the priming field is generated in temporal relationship with the therapeutic neuromodulation field.

In Example 10, the subject matter of Example 9 optionally includes wherein the temporal relationship is varied during execution of the testing program and custom priming program to determine a minimal energy expenditure of the neuromodulation signaling.

Example 11 is directed to a method for configuring a neuromodulation device, the method comprising: receiving, by the neuromodulation device, testing program configuration instructions including therapeutic neuromodulation field-setting parameters; determining, by the neuromodulation device, a custom priming program in response to the testing program configuration instructions, wherein the custom priming program controls the neuromodulation device to generate a priming field with specific correspondence to the therapeutic neuromodulation field to be produced by the testing program; executing the custom priming program to generate a priming field to produce a priming effect in priming-targeted neural tissue, wherein the priming effect causes a change in sensitization of the priming-targeted neural tissue to a therapeutic neuromodulation field; and executing the testing program to generate the therapeutic neuromodulation field to produce a therapeutic effect in therapy-targeted neural tissue.

In Example 12, the subject matter of Example 11 optionally includes wherein the priming program is initiated prior to execution of the testing program.

In Example 13, the subject matter of any one or more of Examples 11-12 optionally include wherein the therapeutic neuromodulation field-setting parameters define a plurality of therapeutic neuromodulation field locations in the therapy-targeted neural tissue, and wherein the custom priming program is adapted to cause the neuromodulation device to produce at least one priming field having specific spatial correspondence to the plurality of therapeutic neuromodulation field locations.

In Example 14, the subject matter of any one or more of Examples 11-13 optionally include adapting the custom priming program, by the neuromodulation device, in response to a result of execution of the testing program to focus the custom priming program on a selected set of the therapeutic neuromodulation field-setting parameters determined to be most effective by execution of the testing program.

In Example 15, the subject matter of any one or more of Examples 11-14 optionally include wherein parameters of the custom priming program are determined by the neuromodulation device by application of predefined decision criteria stored locally on the neuromodulation device.

In Example 16, the subject matter of any one or more of Examples 11-15 optionally include wherein the custom priming program is determined by the neuromodulation device based on receiving the custom priming program from a remote device.

In Example 17, the subject matter of any one or more of Examples 11-16 optionally include wherein the custom priming program is executed during execution of the testing program.

In Example 18, the subject matter of Example 17 optionally includes wherein the testing program defines a plurality of distinct therapeutic neuromodulation field locations in the therapy-targeted neural tissue to be targeted at corresponding different times, including a first location and a second location; and wherein the custom priming program is to cause the neuromodulation device to direct the priming field to the second location during application of the therapeutic neuromodulation field to the first location.

In Example 19, the subject matter of any one or more of Examples 17-18 optionally include wherein the neuromodulation device is configured to determine the custom priming program based on the testing program such that the priming field is generated in temporal relationship with the therapeutic neuromodulation field.

In Example 20, the subject matter of Example 19 optionally includes wherein the temporal relationship is varied during execution of the testing program and custom priming program to determine a minimal energy expenditure of the neuromodulation signaling.

This Summary is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
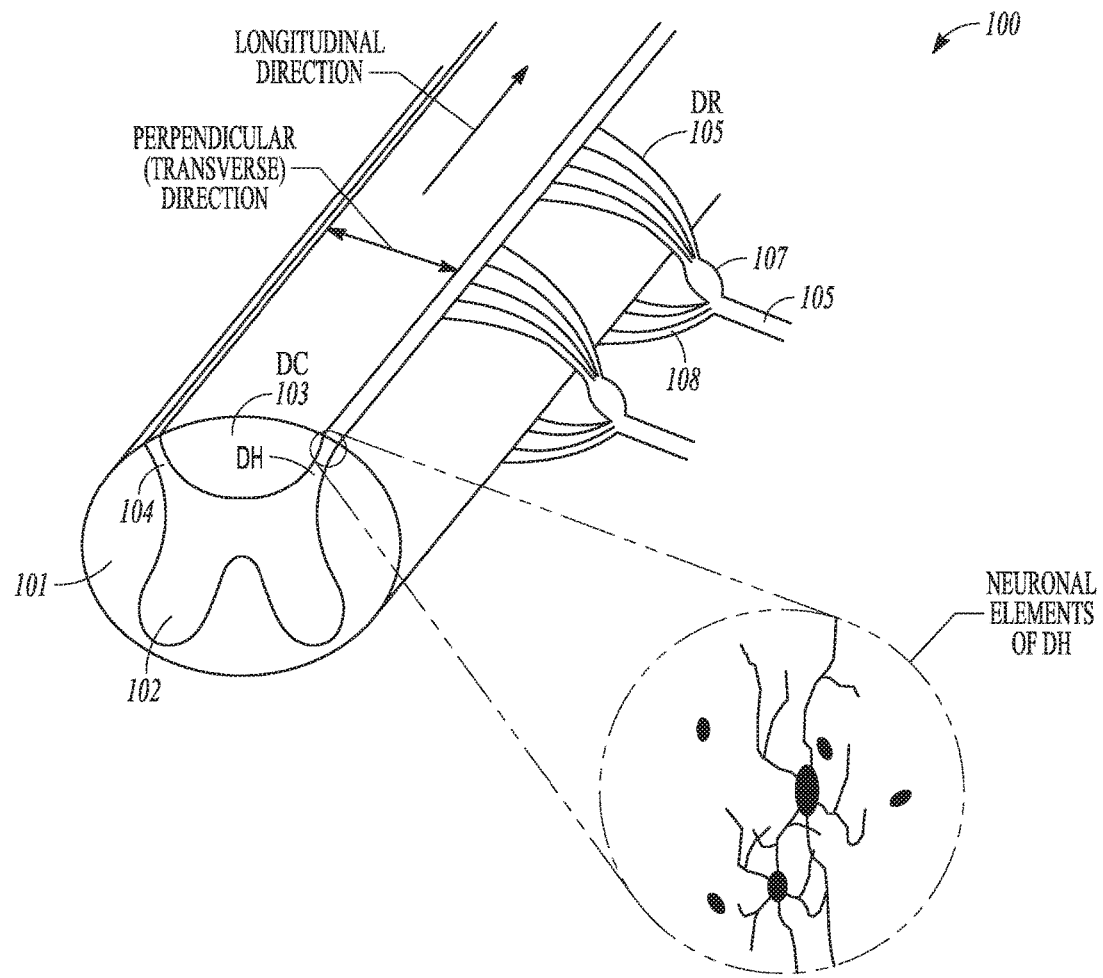
FIG. 1 illustrates a portion of a spinal cord.

The following detailed description of the present subject matter refers to the accompanying drawings which show, by way of illustration, specific aspects and embodiments in which the present subject matter may be practiced. These embodiments are described in sufficient detail to enable those skilled in the art to practice the present subject matter. Other embodiments may be utilized and structural, logical, and electrical changes may be made without departing from the scope of the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

Sub-perception neuromodulation is neuromodulation that can be therapeutically effective. Thus, the therapeutic effects of the sub-perception neuromodulation can be perceived. However, unlike conventional SCS therapy which can cause sensations (e.g. paresthesia) when the therapy is delivered, the energy of the delivered sub-perception neuromodulation field is not perceptible apart from any perceptible therapeutic effects.

Sub-perception SCS may typically have a wash-in period on the order of about one day. Thus, when the programmed neuromodulation parameters are changed to change the location of the neuromodulation field, the patient may not be able to determine the effect that the changes have on pain for a day or so. This makes it difficult quickly titrate the neuromodulation field of the sub-perception SCS to provide effective pain relief to the patient.

Various embodiments may be used to provide a faster therapeutic response (e.g. pain relief) to the sub-perception neuromodulation. Faster responses to sub-perception neuromodulation may be useful in order to find an effective location (sweet-spot) for the neuromodulation field within an office visit. The sweet spot may be a relatively optimal location for the neuromodulation field as it is more optimal than other locations tested.

Various embodiments may deliver a low intensity field in preparation for testing for and finding the sweet-spot for the sub-perception neuromodulation field. The preparatory, lower intensity field may be referred to herein as a priming field, as it is used to prime the neural tissue to induce a faster response to the sub-perception neuromodulation field. Thus, priming the neural tissue enables faster pain relief feedback from the patient during the search for the neuromodulation field sweet spot.

While priming neural tissue for purposes of testing sub-perception neuromodulation is specifically discussed as an example, priming neural tissue can be applied to lower the stimulation energy required for both sub-perception neuromodulation and supra-perception neuromodulation, and expedite the response to both test and therapeutic modulations. The energy of the supra-perception neuromodulation delivered to the neuromodulation field is perceptible. The therapeutic neuromodulation is delivered to treat a condition indicated for at least one type of neuromodulation. A test neuromodulation includes neuromodulation delivered for the purposes of testing effectiveness of a therapeutic neuromodulation and/or setting parameters for the therapeutic neuromodulation. For example, a patient suffering from certain types of pain may be indicated for spinal cord neuromodulation as the therapeutic neuromodulation. In similar fashion, a patient suffering from Parkinson's disease (PD), dystonia, essential tremor (ET), or other neurologic disorder of the brain may be indicated for DBS, such as subthalamic nucleus stimulation (STN) or globus pallidus internus (GPi) stimulation. A test neuromodulation may be delivered to find the sweet spot for the neuromodulation field and/or other parameters controlling delivery of the therapeutic neuromodulation, such as pulse waveform, pulse duration, pulse repetition rate, pulse amplitude, and the like. Depending on various factors such as patient preference and effectiveness, sub-perception neuromodulation and/or supra-perception neuromodulation may be delivered as the therapeutic neuromodulation. The target tissue of the neuromodulation can be primed for the test neuromodulation and/or the therapeutic neuromodulation. While specifically discussed for test neuromodulation delivered in preparation for therapeutic sub-perception neuromodulation, various embodiments can include applying the priming techniques (including timing of the priming relative to the therapeutic neuromodulation) discussed in this document to test neuromodulation delivered in preparation for therapeutic sub-perception neuromodulation, test neuromodulation delivered in preparation for therapeutic supra-perception neuromodulation, therapeutic sub-perception neuromodulation, and therapeutic supra-perception neuromodulation.

As some embodiments described herein involve Spinal Cord Stimulation (SCS, also referred to as spinal cord neuromodulation), a brief description of the physiology of the spinal cord is provided herein to assist the reader. FIG. 1 illustrates, by way of example, a portion of a spinal cord 100 including white matter 101 and gray matter 102 of the spinal cord. The gray matter 102 includes cell bodies, synapse, dendrites, and axon terminals. Thus, synapses are located in the gray matter. White matter 101 includes myelinated axons that connect gray matter areas. A typical transverse section of the spinal cord includes a central "butterfly" shaped central area of gray matter 102 substantially surrounded by an ellipse-shaped outer area of white matter 101. The white matter of the dorsal column (DC) 103 includes mostly large myelinated axons that form afferent fibers that run in an axial direction. The dorsal portions of the "butterfly" shaped central area of gray matter are referred to as dorsal horns (DH) 104. In contrast to the DC fibers that run in an axial direction, DH fibers can be oriented in many directions, including perpendicular to the longitudinal axis of the spinal cord. Examples of spinal nerves 105 are also illustrated, including a dorsal root (DR) 105, dorsal root ganglion 107 and ventral root 108. The dorsal root 105 mostly carries sensory signals into the spinal cord, and the ventral root functions as an efferent motor root. The dorsal and ventral roots join to form mixed spinal nerves 105.

SCS has been used to alleviate pain. A therapeutic goal for conventional SCS programming has been to maximize stimulation (i.e., recruitment) of the DC fibers that run in the white matter along the longitudinal axis of the spinal cord and minimal stimulation of other fibers that run perpendicular to the longitudinal axis of the spinal cord (dorsal root fibers, predominantly), as illustrated in FIG. 1. The white matter of the DC includes mostly large myelinated axons that form afferent fibers. While the full mechanisms of pain relief are not well understood, it is believed that the perception of pain signals is inhibited via the gate control theory of pain, which suggests that enhanced activity of innocuous touch or pressure afferents via electrical stimulation creates interneuronal activity within the DH of the spinal cord that releases inhibitory neurotransmitters (Gamma-Aminobutyric Acid (GABA), glycine), which in turn, reduces the hypersensitivity of wide dynamic range (WDR) sensory neurons to noxious afferent input of pain signals traveling from the dorsal root (DR) neural fibers that innervate the pain region of the patient, as well as treating general WDR ectopy. Consequently, the large sensory afferents of the DC nerve fibers have been targeted for stimulation at an amplitude that provides pain relief. Current implantable neuromodulation systems typically include electrodes implanted adjacent, i.e., resting near, or upon the dura, to the dorsal column of the spinal cord of the patient and along a longitudinal axis of the spinal cord of the patient.

Activation of large sensory DC nerve fibers also typically creates the paresthesia sensation that often accompanies conventional SCS therapy. Although alternative or artifactual sensations, such as paresthesia, are usually tolerated relative to the sensation of pain, patients sometimes report these sensations to be uncomfortable, and therefore, they can be considered an adverse side-effect to neuromodulation therapy in some cases.

Some embodiments deliver sub-perception therapy that is therapeutically effective to treat pain, for example, but the patient does not sense the delivery of the neuromodulation field (e.g. paresthesia). Sub-perception therapy may be provided using higher frequency neuromodulation (e.g. about 1500 Hz or above) of the spinal cord. Sub-perception neuromodulation may also be provided through neuromodulation field shaping (e.g., using multiple independent current control, or MICC), and temporal shaping of pulse train (e.g., burst, longer pulses). It appears that these higher frequencies may effectively block the transmission of pain signals in the afferent fibers in the DC. Some embodiments herein selectively modulate DH tissue or DR tissue over DC tissue to provide sub-perception therapy. Such selective neuromodulation may be delivered at lower frequencies. For example, the selective neuromodulation may be delivered at frequencies less than 1,200 Hz. The selective neuromodulation may be delivered at frequencies less than 1,000 Hz in some embodiments. In some embodiments, the selective neuromodulation may be delivered at frequencies less than 500 Hz. In some embodiments, the selective neuromodulation may be delivered at frequencies less than 350 Hz. In some embodiments, the selective neuromodulation may be delivered at frequencies less than 130 Hz. The selective neuromodulation may be delivered at low frequencies (e.g. as low as 2 Hz). The selective neuromodulation may be delivered even without pulses (e.g. 0 Hz) to modulate some neural tissue. By way of example and not limitation, the selective neuromodulation may be delivered within a frequency range selected from the following frequency ranges: 2 Hz to 1,200 Hz; 2 Hz to 1,000 Hz, 2 Hz to 500 Hz; 2 Hz to 350 Hz; or 2 Hz to 130 Hz. Systems may be developed to raise the lower end of any these ranges from 2 Hz to other frequencies such as, by way of example and not limitation, 10 Hz, 20 Hz, 50 Hz or 100 Hz. By way of example and not limitation, it is further noted that the selective neuromodulation may be delivered with a duty cycle, in which stimulation (e.g. a train of pulses) is delivered during a Stimulation ON portion of the duty cycle, and is not delivered during a Stimulation OFF portion of the duty cycle. By way of example and not limitation, the duty cycle may be about 10%±5%, 20%±5%, 30%±5%, 40%±5%, 50%±5% or 60%±5%. For example, a burst of pulses for 10 ms during a Stimulation ON portion followed by 15 ms without pulses corresponds to a 40% duty cycle.

While SCS is specifically discussed as an example of neuromodulation therapy, various embodiments can also include applying the priming techniques including timing of delivery discussed in this document to Peripheral Nerve Stimulation (PNS) therapies. For example, sub-perception PNS may be applied to alleviate pain. Various embodiments include priming the neural tissue at target locations for delivering the neuromodulation where required intensity of the neuromodulation for testing and/or therapeutic purposes may be lowered.

Figure 2:
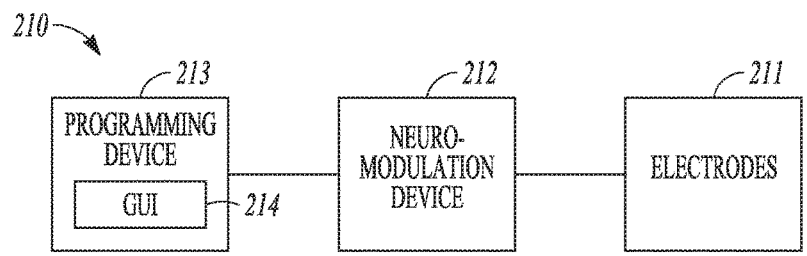
FIG. 2 illustrates, by way of example, an embodiment of a neuromodulation system.

FIG. 2 illustrates an embodiment of a neuromodulation system. The illustrated system 210 includes electrodes 211, a neuromodulation device 212, and a programming device 213. The electrodes 211 are configured to be placed on or near one or more neural targets in a patient. The electrodes 211 may form part of an electrode arrangement. The neuromodulation device 212 is configured to be electrically connected to electrodes 211 and deliver neuromodulation energy, such as in the form of electrical pulses, to the one or more neural targets though electrodes 211. The delivery of the neuromodulation is controlled using a plurality of neuromodulation parameters, such as neuromodulation parameters specifying the electrical pulses and a selection of electrodes through which each of the electrical pulses is delivered. In various embodiments, at least some parameters of the plurality of neuromodulation parameters are programmable by a user, such as a physician or other caregiver. The programming device 213 provides the user with accessibility to the user-programmable parameters. In various embodiments, the programming device 213 is configured to be communicatively coupled to neuromodulation device via a wired or wireless link. In various embodiments, the programming device 213 includes a graphical user interface (GUI) 214 that allows the user to set and/or adjust values of the user-programmable neuromodulation parameters.

In various embodiments, the neuromodulation system 210 can include implantable and external elements. For example, the neuromodulation device 212 can be an implantable neuromodulation device, the electrodes 211 can include electrodes in one or more implantable lead and/or the implantable neuromodulation device, and the programming device can be an external programming device configured to be communicatively coupled to the implantable neuromodulation device via telemetry, as further discussed with reference to FIGS. 5 and 6. In another example, the neuromodulation device 212 can be an external neuromodulation device such as a Transcutaneous Electrical Neural Stimulation (TENS) device, the electrodes 211 can include surface electrodes such as skin patch electrodes, and the programming device can be an external programming device configured to be communicatively coupled to the implantable neuromodulation device via a wired or wireless link, or integrated with the external neuromodulation device. In still another example, the neuromodulation device 212 can be an external neuromodulation device, the electrodes 211 can include percutaneous electrodes, and the programming device can be an external programming device configured to be communicatively coupled to the implantable neuromodulation device via a wired or wireless link, or integrated with the external neuromodulation device. In various embodiments, an external neuromodulation device with surface and/or percutaneous electrodes can be used, for example, for delivering a test neuromodulation, delivering a therapeutic neuromodulation during a trial period, and delivering a short-term therapeutic neuromodulation.

In one embodiment, an external neuromodulation device with surface electrodes can be used during a trial period prior to a potential implantation of an implantable SCS system. A skin patch including the surface electrodes is placed over the patient's spine near the region where percutaneous electrodes will be placed for use during the trial period. The external neuromodulation device such as a dedicated External Trial Stimulator (ETC) and/or an external TENS device is used to prime the neural tissue before the trial period using one or more electrodes selected from the surface electrodes. This allows the programming of the external neuromodulation device for delivering therapeutic neuromodulation through the percutaneous electrodes to be performed with reduced wash-in time, such as immediately following the placement of the percutaneous electrodes.

Figure 3:
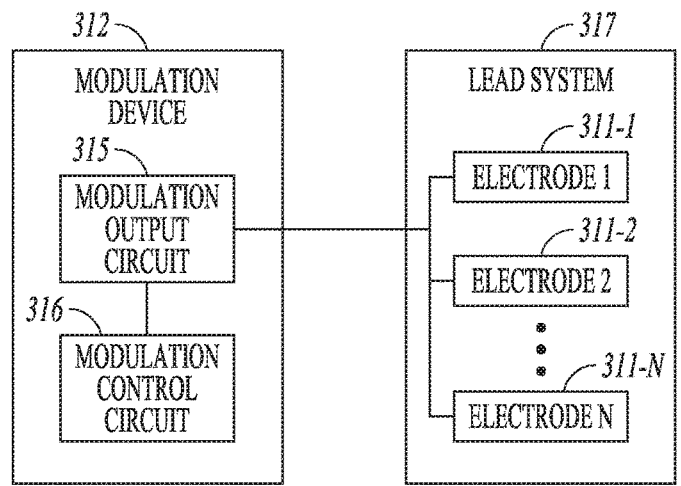
FIG. 3 illustrates, by way of example, an embodiment of a neuromodulation device, such as may be implemented in the neuromodulation system of FIG. 2.

FIG. 3 illustrates an embodiment of a neuromodulation device 312, such as may be implemented in the neuromodulation system 210 of FIG. 2. The illustrated embodiment of the neuromodulation device 312 includes a neuromodulation output circuit 315 and a neuromodulation control circuit 316. Those of ordinary skill in the art will understand that the neuromodulation system 210 may include additional components such as sensing circuitry for patient monitoring and/or feedback control of the therapy, telemetry circuitry and power. The neuromodulation output circuit 315 produces and delivers neuromodulation pulses. The neuromodulation control circuit 316 controls the delivery of the neuromodulation pulses using the plurality of neuromodulation parameters. The combination of the neuromodulation output circuit 315 and neuromodulation control circuit 316 may collectively be referred to as a pulse generator. The lead system 317 includes one or more leads each configured to be electrically connected to neuromodulation device 312 and a plurality of electrodes 311-1 to 311-N (where N≥2) distributed in an electrode arrangement using the one or more leads. Each lead may have an electrode array consisting of two or more electrodes, which also may be referred to as contacts. Multiple leads may provide multiple electrode arrays to provide the electrode arrangement. Each electrode is a single electrically conductive contact providing for an electrical interface between neuromodulation output circuit 315 and tissue of the patient. The neuromodulation pulses are each delivered from the neuromodulation output circuit 315 through a set of electrodes selected from the electrodes 311-1 to 311-N. The number of leads and the number of electrodes on each lead may depend on, for example, the distribution of target(s) of the neuromodulation and the need for controlling the distribution of electric field at each target. In one embodiment, by way of example and not limitation, the lead system includes two leads each having eight electrodes.

The neuromodulation system may be configured to modulate spinal target tissue, brain tissue, or other neural tissue. The configuration of electrodes used to deliver electrical pulses to the targeted tissue constitutes an electrode configuration, with the electrodes capable of being selectively programmed to act as anodes (positive), cathodes (negative), or left off (zero). In other words, an electrode configuration represents the polarity being positive, negative, or zero. Other parameters that may be controlled or varied include the amplitude, pulse width, and rate (or frequency) of the electrical pulses. Each electrode configuration, along with the electrical pulse parameters, can be referred to as a "neuromodulation parameter set." Each set of neuromodulation parameters, including fractionalized current distribution to the electrodes (as percentage cathodic current, percentage anodic current, or off), may be stored and combined into a neuromodulation program that can then be used to modulate multiple regions within the patient.

The number of electrodes available combined with the ability to generate a variety of complex electrical pulses, presents a huge selection of neuromodulation parameter sets to the clinician or patient. For example, if the neuromodulation system to be programmed has sixteen electrodes, millions of neuromodulation parameter sets may be available for programming into the neuromodulation system. Furthermore, for example SCS systems may have thirty-two electrodes which exponentially increases the number of neuromodulation parameters sets available for programming. To facilitate such selection, the clinician generally programs the neuromodulation parameters sets through a computerized programming system to allow the optimum neuromodulation parameters to be determined based on patient feedback or other means and to subsequently program the desired neuromodulation parameter sets.

Conventional programming for SCS therapy uses paresthesia to select an appropriate neuromodulation parameter set. The paresthesia induced by the neuromodulation and perceived by the patient should be located in approximately the same place in the patient's body as the pain that is the target of treatment. When leads are implanted within the patient, an operating room (OR) mapping procedure may be performed to apply electrical neuromodulation to test placement of the leads and/or electrodes, thereby assuring that the leads and/or electrodes are implanted in effective locations within the patient. According to various embodiments, programming for sub-perception neuromodulation may prime the neural tissue to provide faster response times to the sub-perception neuromodulation as part of an OR mapping procedure.

Once the leads are correctly positioned, a fitting procedure, which may be referred to as a navigation session, may be performed to program the external control device, and if applicable the neuromodulation device, with a set of neuromodulation parameters that best addresses the painful site. Thus, the navigation session may be used to pinpoint the volume of activation (VOA) or areas correlating to the pain. The procedure may be implemented to target the tissue during implantation, or after implantation should the leads gradually or unexpectedly move that would otherwise relocate the neuromodulation energy away from the target site. By reprogramming the neuromodulation device (typically by independently varying the neuromodulation energy on the electrodes), the VOA can often be moved back to the effective pain site without having to re-operate on the patient in order to reposition the lead and its electrode array. According to various embodiments, a navigation session for sub-perception neuromodulation may prime the neural tissue to provide faster response times to the sub-perception neuromodulation.

Although various embodiments described in this document prime neural tissue to provide faster responses to sub-perception neuromodulation in order to perform faster OR mapping or navigation sessions, the present subject matter is not limited to such programming. By way of example and not limitation, some embodiment may prime the neural tissue before delivering the sub-perception neuromodulation therapy to the neural tissue simply to reduce the wash-in time of the therapy. Thus, by way of example, a patient may obtain pain relief much quicker with the primed neural tissue than without the primed neural tissue.

Figure 4:
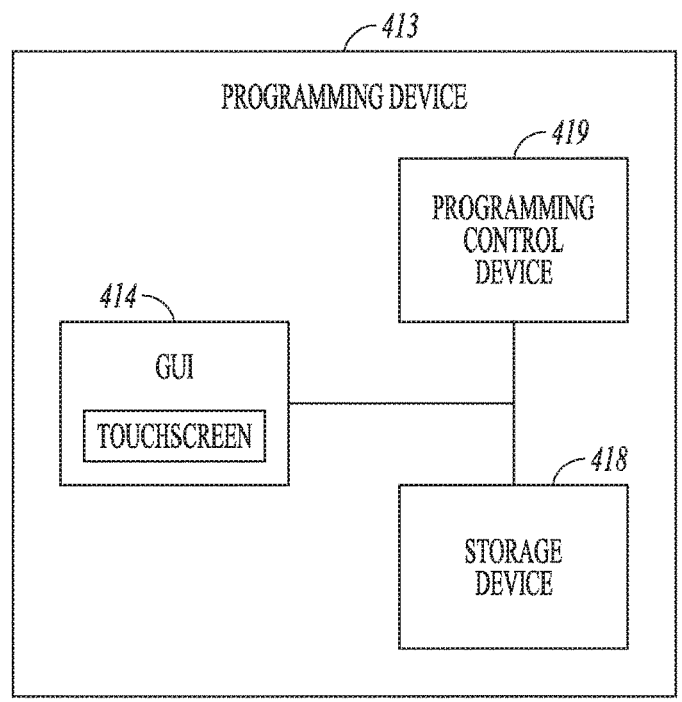
FIG. 4 illustrates, by way of example, an embodiment of a programming device, such as may be implemented as the programming device in the neuromodulation system of FIG. 2.

FIG. 4 illustrates an embodiment of a programming device 413, such as may be implemented as the programming device 213 in the neuromodulation system of FIG. 2. The programming device 413 includes a storage device 418, a programming control circuit 419, and a GUI 414. The programming control circuit 419 generates the plurality of neuromodulation parameters that controls the delivery of the neuromodulation pulses according to the pattern of the neuromodulation pulses. In various embodiments, the GUI 414 includes any type of presentation device, such as interactive or non-interactive screens, and any type of user input devices that allow the user to program the neuromodulation parameters, such as touchscreen, keyboard, keypad, touchpad, trackball, joystick, and mouse. The storage device 418 may store, among other things, neuromodulation parameters to be programmed into the neuromodulation device. The programming device 413 may transmit the plurality of neuromodulation parameters to the neuromodulation device. In some embodiments, the programming device 413 may transmit power to the neuromodulation device. The programming control circuit 419 may generate the plurality of neuromodulation parameters. In various embodiments, the programming control circuit 419 may check values of the plurality of neuromodulation parameters against safety rules to limit these values within constraints of the safety rules.

In various embodiments, circuits of neuromodulation, including its various embodiments discussed in this document, may be implemented using a combination of hardware, software and firmware. For example, the circuit of a GUI, neuromodulation control circuit, and programming control circuit, including their various embodiments discussed in this document, may be implemented using an application-specific circuit constructed to perform one or more particular functions or a general-purpose circuit programmed to perform such function(s). Such a general-purpose circuit includes, but is not limited to, a microprocessor or a portion thereof, a microcontroller or portions thereof, and a programmable logic circuit or a portion thereof.

Figure 5:
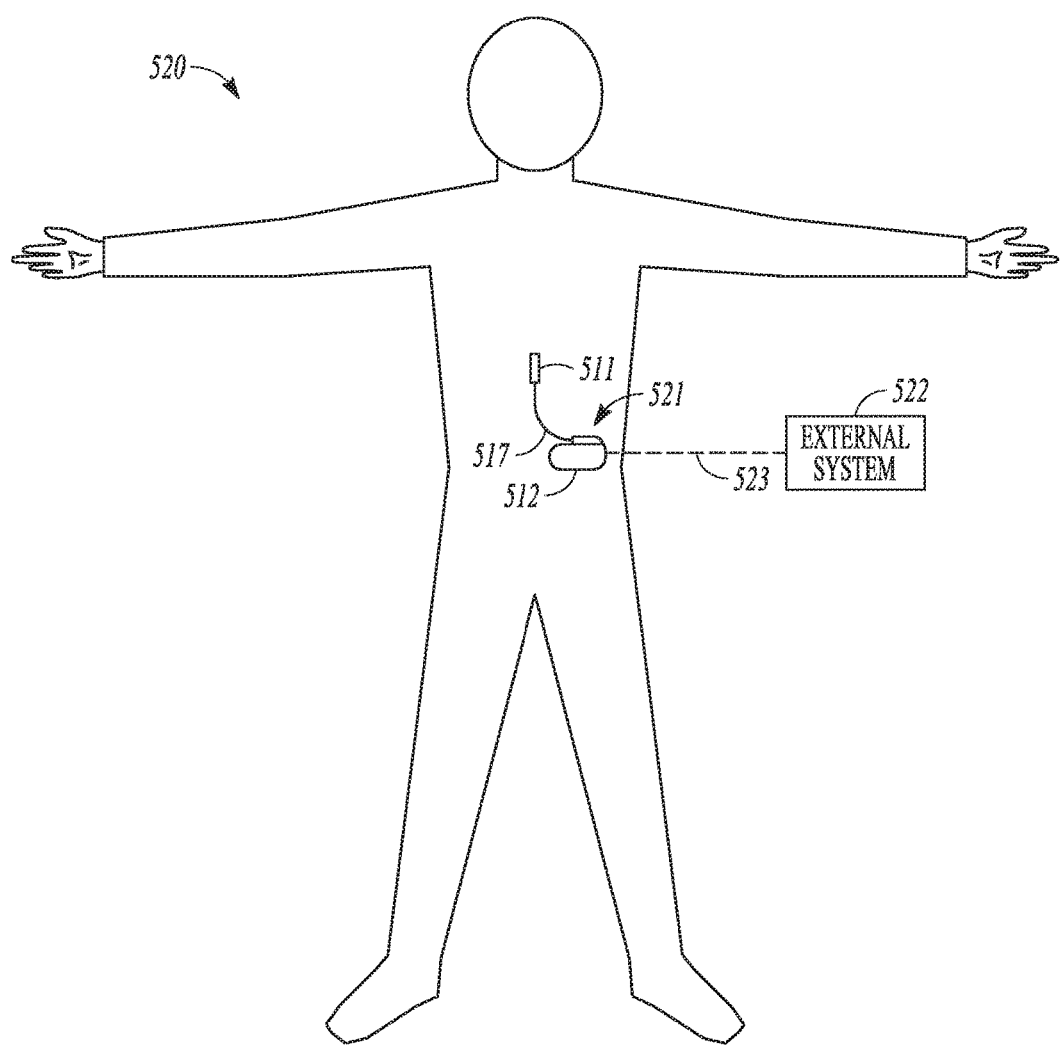
FIG. 5 illustrates, by way of example, an implantable neuromodulation system and portions of an environment in which system may be used.

FIG. 5 illustrates, by way of example, an implantable neuromodulation system and portions of an environment in which system may be used. The system is illustrated for implantation near the spinal cord. However, neuromodulation system may be configured to modulate other neural targets such as may be useful for delivering other therapies. The system 520 includes an implantable system 521, an external system 522, and a telemetry link 523 providing for wireless communication between implantable system 521 and external system 522. The implantable system is illustrated as being implanted in the patient's body. The implantable system 521 includes an implantable neuromodulation device (also referred to as an implantable pulse generator, or IPG) 512, a lead system 517, and electrodes 511. The lead system 517 includes one or more leads each configured to be electrically connected to the neuromodulation device 512 and a plurality of electrodes 511 distributed in the one or more leads. In various embodiments, the external system 402 includes one or more external (non-implantable) devices each allowing a user (e.g. a clinician or other caregiver and/or the patient) to communicate with the implantable system 521. In some embodiments, the external system 522 includes a programming device intended for a clinician or other caregiver to initialize and adjust settings for the implantable system 521 and a remote control device intended for use by the patient. For example, the remote control device may allow the patient to turn a therapy on and off and/or adjust certain patient-programmable parameters of the plurality of neuromodulation parameters.

The neuromodulation lead(s) of the lead system 517 may be placed adjacent, i.e., resting near, or upon the dura, adjacent to the spinal cord area to be stimulated. For example, the neuromodulation lead(s) may be implanted along a longitudinal axis of the spinal cord of the patient. Due to the lack of space near the location where the neuromodulation lead(s) exit the spinal column, the implantable neuromodulation device 512 may be implanted in a surgically-made pocket either in the abdomen or above the buttocks, or may be implanted in other locations of the patient's body. The lead extension(s) may be used to facilitate the implantation of the implantable neuromodulation device 512 away from the exit point of the neuromodulation lead(s).

Figure 6:
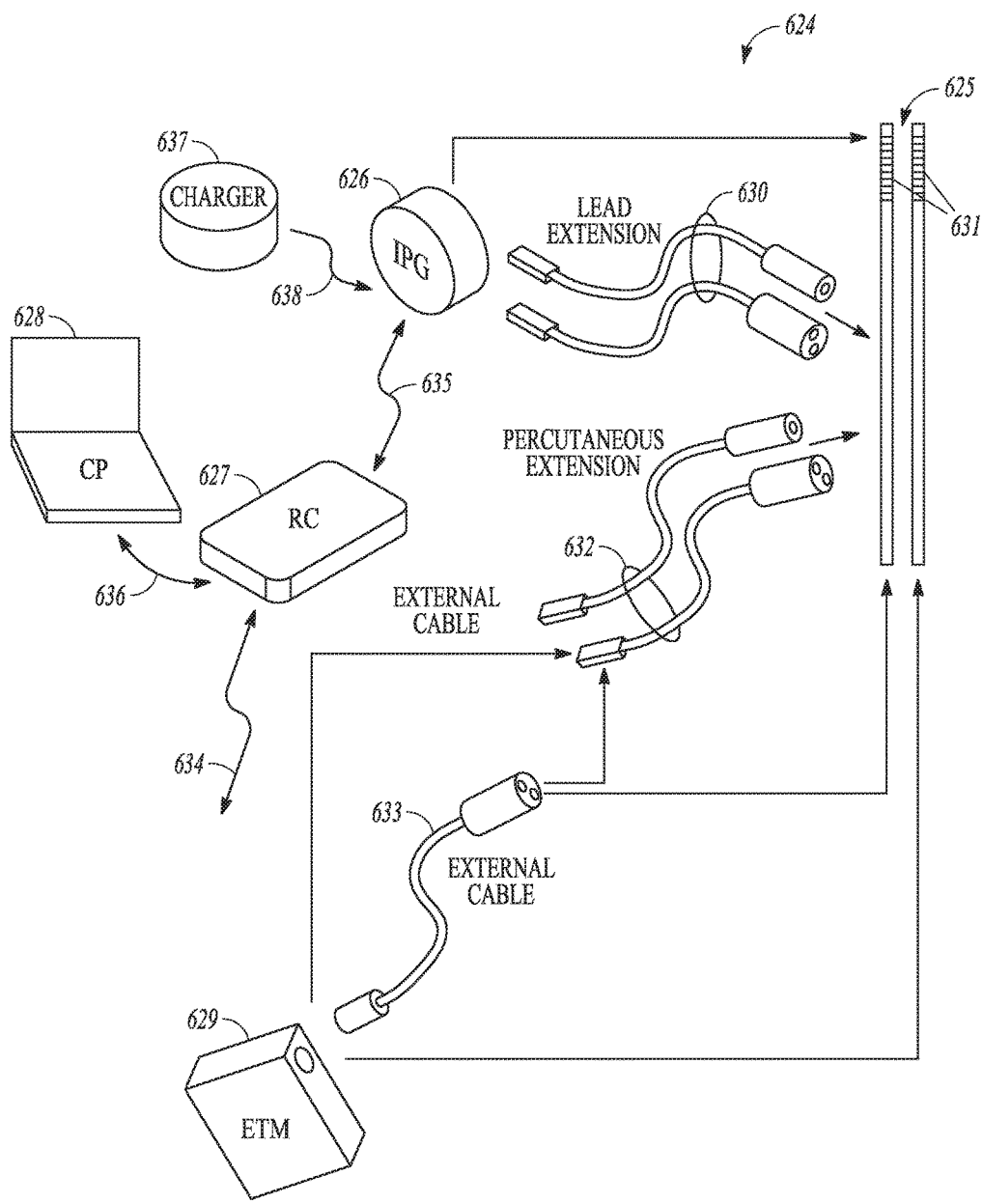
FIG. 6 illustrates, by way of example, an embodiment of a Spinal Cord Stimulation (SCS) system, which also may be referred to as a Spinal Cord Neuromodulation (SCM) system.

FIG. 6 illustrates, by way of example, an embodiment of a SCS system, which also may be referred to as a Spinal Cord Neuromodulation (SCM) system. The SCS system 624 may generally include a plurality (illustrated as two) of implantable neuromodulation leads 625, an implantable pulse generator (IPG) 626, an external remote controller RC 627, a clinician's programmer (CP) 628, and an external trial modulator (ETM) 629. The IPG 626 may be physically connected via one or more percutaneous lead extensions 630 to the neuromodulation leads 625, which carry a plurality of electrodes 631. As illustrated, the neuromodulation leads 625 may be percutaneous leads with the electrodes arranged in-line along the neuromodulation leads. Any suitable number of neuromodulation leads can be provided, including only one, as long as the number of electrodes is greater than two (including the IPG case function as a case electrode) to allow for lateral steering of the current. Alternatively, a surgical paddle lead can be used in place of one or more of the percutaneous leads. The IPG 626 includes pulse generation circuitry, also referred to as a pulse generator, that delivers electrical neuromodulation energy in the form of a pulsed electrical waveform (i.e., a temporal series of electrical pulses) to the electrodes in accordance with a set of neuromodulation parameters.

The ETM 629 may also be physically connected via the percutaneous lead extensions 632 and external cable 633 to the neuromodulation leads 625. The ETM 629 may have similar pulse generation circuitry as the IPG 626 to deliver electrical neuromodulation energy to the electrodes accordance with a set of neuromodulation parameters. The ETM 629 is a non-implantable device that is used on a trial basis after the neuromodulation leads 625 have been implanted and prior to implantation of the IPG 626, to test the responsiveness of the neuromodulation that is to be provided. Functions described herein with respect to the IPG 626 can likewise be performed with respect to the ETM 629.

The RC 627 may be used to telemetrically control the ETM 629 via a bi-directional RF communications link 634.

The RC 627 may be used to telemetrically control the IPG 626 via a bi-directional RF communications link 635. Such control allows the IPG 626 to be turned on or off and to be programmed with different neuromodulation parameter sets. The IPG 626 may also be operated to modify the programmed neuromodulation parameters to actively control the characteristics of the electrical neuromodulation energy output by the IPG 626. A clinician may use the CP 628 to program neuromodulation parameters into the IPG 626 and ETM 629 in the operating room and in follow-up sessions.

The CP 628 may indirectly communicate with the IPG 626 or ETM 629, through the RC 627, via an IR communications link 636 or other link. The CP 628 may directly communicate with the IPG 626 or ETM 629 via an RF communications link or other link (not shown). The clinician detailed neuromodulation parameters provided by the CP 628 may also be used to program the RC 627, so that the neuromodulation parameters can be subsequently modified by operation of the RC 627 in a stand-alone mode (i.e., without the assistance of the CP 628). Various devices may function as the CP 628. Such devices may include portable devices such as a lap-top personal computer, mini-computer, personal digital assistant (PDA), tablets, phones, or a remote control (RC) with expanded functionality. Thus, the programming methodologies can be performed by executing software instructions contained within the CP 628. Alternatively, such programming methodologies can be performed using firmware or hardware. In any event, the CP 628 may actively control the characteristics of the electrical neuromodulation generated by the IPG 626 to allow the desired parameters to be determined based on patient feedback or other feedback and for subsequently programming the IPG 626 with the desired neuromodulation parameters. To allow the user to perform these functions, the CP 628 may include a user input device (e.g., a mouse and a keyboard), and a programming display screen housed in a case. In addition to, or in lieu of, the mouse, other directional programming devices may be used, such as a trackball, touchpad, joystick, touch screens or directional keys included as part of the keys associated with the keyboard. An external device (e.g. CP) may be programmed to provide display screen(s) that allow the clinician to, among other functions, to select or enter patient profile information (e.g., name, birth date, patient identification, physician, diagnosis, and address), enter procedure information (e.g., programming/follow-up, implant trial system, implant IPG, implant IPG and lead(s), replace IPG, replace IPG and leads, replace or revise leads, explant, etc.), generate a pain map of the patient, define the configuration and orientation of the leads, initiate and control the electrical neuromodulation energy output by the neuromodulation leads, and select and program the IPG with neuromodulation parameters in both a surgical setting and a clinical setting.

An external charger 637 may be a portable device used to transcutaneously charge the IPG via a wireless link such as an inductive link 638. Once the IPG has been programmed, and its power source has been charged by the external charger or otherwise replenished, the IPG may function as programmed without the RC or CP being present.

Figure 7:
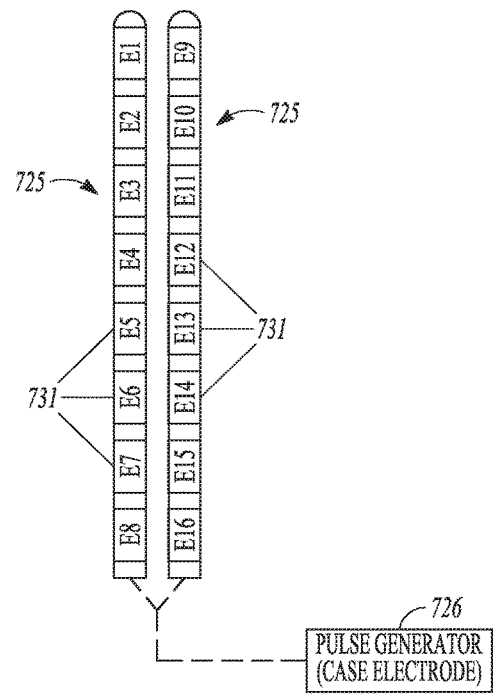
FIG. 7 illustrates, by way of example, some features of the neuromodulation leads and a pulse generator.

FIG. 7 illustrates, by way of example, some features of the neuromodulation leads 725 and a pulse generator 726. The pulse generator 726 may be an implantable device (IPG) or may be an external device such as may be used to test the electrodes during an implantation procedure. In the illustrated example, one of the neuromodulation leads has eight electrodes 731 (labeled E1-E8), and the other neuromodulation lead has eight electrodes 731 (labeled. E9-E16). The actual number and shape of leads and electrodes may vary for the intended application. An implantable pulse generator (IPG) may include an outer case for housing the electronic and other components. The outer case may be composed of an electrically conductive, biocompatible material, such as titanium, that forms a hermetically-sealed compartment wherein the internal electronics are protected from the body tissue and fluids. In some cases, the outer case may serve as an electrode (e.g. case electrode). The IPG may include electronic components, such as a controller/processor (e.g., a microcontroller), memory, a battery, telemetry circuitry, monitoring circuitry, neuromodulation output circuitry, and other suitable components known to those skilled in the art. The microcontroller executes a suitable program stored in memory, for directing and controlling the neuromodulation performed by IPG.

Electrical neuromodulation energy is provided to the electrodes in accordance with a set of neuromodulation parameters programmed into the pulse generator. The electrical neuromodulation energy may be in the form of a pulsed electrical waveform. Such neuromodulation parameters may comprise electrode combinations, which define the electrodes that are activated as anodes (positive), cathodes (negative), and turned off (zero), percentage of neuromodulation energy assigned to each electrode (fractionalized electrode configurations), and electrical pulse parameters, which define the pulse amplitude (measured in milliamps or volts depending on whether the pulse generator supplies constant current or constant voltage to the electrode array), pulse width (measured in microseconds), pulse rate (measured in pulses per second), and burst rate (measured as the neuromodulation on duration X and neuromodulation off duration Y). The electrical pulse parameters may define an intermittent neuromodulation with "on" periods of time where a train of two or more pulses are delivered and "off" periods of time where pulses are not delivered. Electrodes that are selected to transmit or receive electrical energy are referred to herein as "activated," while electrodes that are not selected to transmit or receive electrical energy are referred to herein as "non-activated."

Electrical neuromodulation occurs between or among a plurality of activated electrodes, one of which may be the IPG case. The system may be capable of transmitting neuromodulation energy to the tissue in a monopolar or multipolar (e.g., bipolar, tripolar, etc.) fashion. Monopolar neuromodulation occurs when a selected one of the lead electrodes is activated along with the case of the IPG, so that neuromodulation energy is transmitted between the selected electrode and case.

Any of the electrodes E1-E16 and the case electrode may be assigned to up to k possible groups or timing "channels." In one embodiment, k may equal four. The timing channel identifies which electrodes are selected to synchronously source or sink current to create an electric field in the tissue to be stimulated. Amplitudes and polarities of electrodes on a channel may vary. In particular, the electrodes can be selected to be positive (anode, sourcing current), negative (cathode, sinking current), or off (no current) polarity in any of the k timing channels. The IPG may be operated in a mode to deliver electrical neuromodulation energy that is therapeutically effective and causes the patient to perceive delivery of the energy (e.g. therapeutically effective to relieve pain with perceived paresthesia), and may be operated in a sub-perception mode to deliver electrical neuromodulation energy that is therapeutically effective and does not cause the patient to perceive delivery of the energy (e.g. therapeutically effective to relieve pain without perceived paresthesia). Some embodiments may use one channel to prime the neural tissue with a sub-perception neuromodulation field, and use another channel to deliver therapeutic sub-perception neuromodulation to the neural tissue.

The IPG may be configured to individually control the magnitude of electrical current flowing through each of the electrodes. For example, a current generator may be configured to selectively generate individual current-regulated amplitudes from independent current sources for each electrode. In some embodiments, the pulse generator may have voltage regulated outputs. While individually programmable electrode amplitudes are desirable to achieve fine control, a single output source switched across electrodes may also be used, although with less fine control in programming. Neuromodulators may be designed with mixed current and voltage regulated devices.

Figures 8, 9:
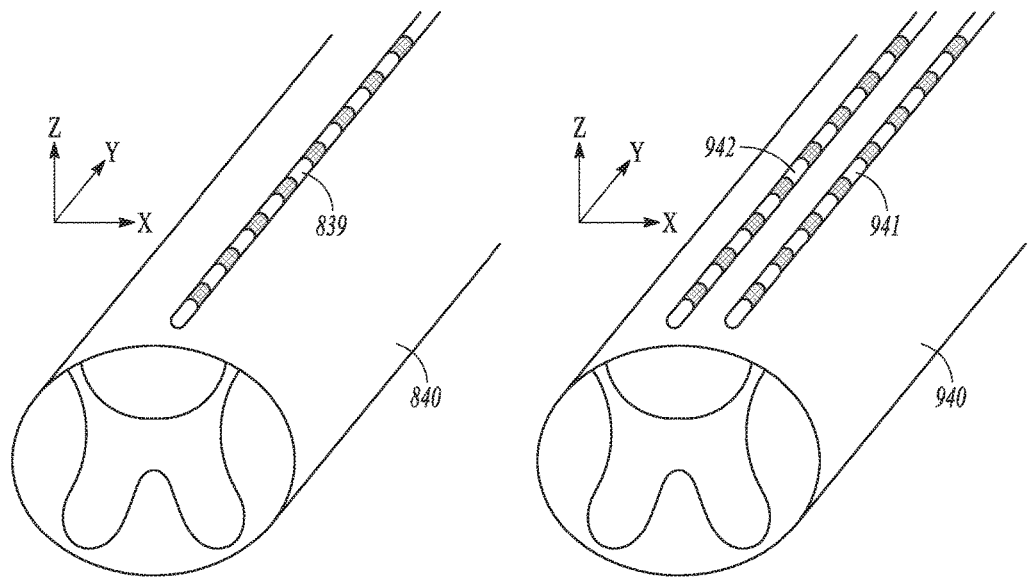
FIG. 8 is a schematic view of a single electrical neuromodulation lead implanted over approximately the longitudinal midline of the patient's spinal cord.
FIG. 9 illustrates an embodiment where an electrical neuromodulation lead has been implanted more laterally with respect to the spinal cord, thereby placing it proximate the dorsal horn of the spinal cord, and the other electrical neuromodulation lead has been implanted more medially with respect to the spinal cord, thereby placing it proximate the dorsal column of the spinal cord.

FIG. 8 is a schematic view of a single electrical neuromodulation lead 839 implanted over approximately the longitudinal midline of the patient's spinal cord 840. FIG. 9 illustrates an embodiment where an electrical neuromodulation lead 941 has been implanted more laterally with respect to the spinal cord, thereby placing it proximate the dorsal horn of the spinal cord, and the other electrical neuromodulation lead 942 has been implanted more medially with respect to the spinal cord, thereby placing it proximate the dorsal column of the spinal cord 940.

It is understood that additional leads or lead paddle(s) may be used, such as may be used to provide a wider electrode arrangement and/or to provide the electrodes closer to dorsal horn elements, and that these electrode arrays also may implement fractionalized current.

Placement of the lead more proximate to the DH than the DC may be desirable to preferentially stimulate DH elements over DC neural elements for a sub-perception therapy. Lead placement may also enable preferential neuromodulation of dorsal roots over other neural elements. Any other plurality of leads or a multiple column paddle lead can also be used. Longitudinal component of the electrical field is directed along the y-axis depicted in FIG. 8, and a transverse component of the electrical field is directed along the x-axis depicted in FIG. 8.

Figure 10:
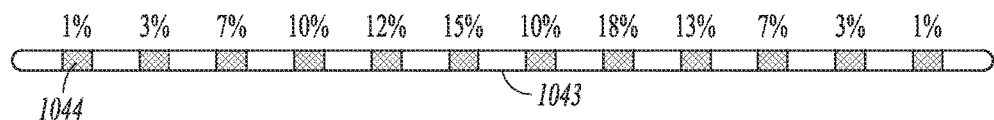
FIG. 10 illustrates a schematic view of the electrical neuromodulation lead showing an example of the fractionalization of the anodic current delivered to the electrodes on the electrical neuromodulation lead.

FIG. 10 is a schematic view of the electrical neuromodulation lead 1043 showing an example of the fractionalization of the anodic current delivered to the electrodes on the electrical neuromodulation lead. These figures illustrate non-fractionalization using monopolar neuromodulation where a case electrode of the IPG is the only cathode, and carries 100% of the cathodic current. The fractionalization of the anodic current shown in FIG. 10 does not deliver an equal amount of current to each electrode 1044, because this embodiment takes into account electrode/tissue coupling differences, which are the differences in how the tissue underlying each electrode reacts to electrical neuromodulation. Also, the ends of the portion of the electrical neuromodulation lead include electrodes having lower gradient in the longitudinal direction. The magnitude of the electrical field tapers down at the ends of the electrical neuromodulation lead. Fractionalization of the current may accommodate variation in the tissue underlying those electrodes. The fractionalization across the electrical neuromodulation lead can vary in any manner as long as the total of fractionalized currents equals 100%. Various embodiments described herein implement a programmed algorithm to determine the appropriate fractionalization to achieve a desired neuromodulation field property.

Neuromodulation thresholds vary from patient to patient and from electrode to electrode within a patient. An electrode/tissue coupling calibration of the electrodes may be performed to account for these different neuromodulation thresholds and provide a more accurate fractionalization of the current between electrodes. For example, perception threshold may be used to normalize the electrodes. The RC or the CP may be configured to prompt the patient to actuate a control element, once paresthesia is perceived by the patient. In response to this user input, the RC or the CP may be configured to respond to this user input by storing the neuromodulation signal strength of the electrical pulse train delivered when the control element is actuated. Other sensed parameter or patient-perceived neuromodulation values (e.g. constant paresthesia, or maximum tolerable paresthesia) may be used to provide the electrode/tissue coupling calibration of the electrodes.

The SCS system may be configured to deliver different electrical fields to achieve a temporal summation of neuromodulation. The electrical fields can be generated respectively on a pulse-by-pulse basis. For example, a first electrical field can be generated by the electrodes (using a first current fractionalization) during a first electrical pulse of the pulsed waveform, a second different electrical field can be generated by the electrodes (using a second different current fractionalization) during a second electrical pulse of the pulsed waveform, a third different electrical field can be generated by the electrodes (using a third different current fractionalization) during a third electrical pulse of the pulsed waveform, a fourth different electrical field can be generated by the electrodes (using a fourth different current fractionalized) during a fourth electrical pulse of the pulsed waveform, and so forth. These electrical fields may be rotated or cycled through multiple times under a timing scheme, where each field is implemented using a timing channel. The electrical fields may be generated at a continuous pulse rate, or may be bursted on and off. Furthermore, the interpulse interval (i.e., the time between adjacent pulses), pulse amplitude, and pulse duration during the electrical field cycles may be uniform or may vary within the electrical field cycle.

Some embodiments are configured to determine a neuromodulation parameter set to create a field shape to provide a broad and uniform neuromodulation field such as may be useful to prime targeted neural tissue with sub-perception neuromodulation. Some embodiments are configured to determine a neuromodulation parameter set to create a field shape to reduce or minimize neuromodulation of non-targeted tissue (e.g. DC tissue). Various embodiments disclosed herein are directed to shaping the neuromodulation field to enhance neuromodulation of some neural structures and diminish neuromodulation at other neural structures. The neuromodulation field may be shaped by using multiple independent current control (MICC) or multiple independent voltage control to guide the estimate of current fractionalization among multiple electrodes and estimate a total amplitude that provide a desired strength. For example, the neuromodulation field may be shaped to enhance the neuromodulation of DH neural tissue and to minimize the neuromodulation of DC tissue. A benefit of MICC is that MICC accounts for various in electrode-tissue coupling efficiency and perception threshold at each individual contact, so that "hot-spot" stimulation is eliminated.

Sub-perception SCS typically does not provide a quick feedback response regarding the effectiveness of the therapy. Rather, it has been observed that a wash-in period (a period of time for a delivered therapy to be therapeutically effective) for the sub-perception SCS is typically about one day. Thus, when the programmed neuromodulation parameters are changed to change the location of the sub-perception neuromodulation field, the patient may not be able to determine the effect that the changes have (e.g. pain relief) for a day or so. This make it difficult quickly titrate the neuromodulation field of the sub-perception SCS to provide effective pain relief to the patient.

It has been observed during research that priming the neural tissue enables faster pain relief feedback from the patient during the search for the neuromodulation field sweet spot. It may be appropriate to consider that priming the neural tissue "warms up" the neural tissue in a manner that reduces the wash-in time. However, neural physiology is complex and it is not currently understood why the primed neural tissue reduces the wash-in time of the sub-perception therapy such that the patient can quickly feel pain relief. It is noted that "priming" is different than conditioning pre-pulses which are delivered immediately before the neuromodulation pulse. A conditioning pre-pulse is timed to make a nerve more susceptible or less susceptible to capture by the immediately subsequent neuromodulation pulse. Thus, a conditioning pre-pulse has a specific relationship to a neuromodulation pulse. In contrast, the prime neuromodulation field extends over a much longer period of time. Further, rather than making neural tissue more or less excitable by a pulse, the prime neuromodulation field reduces a wash-in time of a therapy to make a patient feel the effects of the therapy (e.g. pain relief) much more quickly than would be felt without the prime field.

Various embodiments may deliver a low intensity, neuromodulation field in preparation to test for and find the sweet-spot for the neuromodulation field. The preparatory, lower intensity field is referred to herein as a prime field, as it is used to prime the neural tissue to be tested to have a quicker response to during the testing for the neuromodulation sweet spot for pain relief. The prime field can be a supra-perception or sub-perception neuromodulation field, but is typically even lower than the therapeutic sub-perception neuromodulation field.

A test region of neural tissue represents a region of tissue that is to be tested for a sweet spot. The test region may include many potential locations for targeting the neuromodulation field. The test region may span along the entire electrode arrangement (e.g. lead(s)) or may be reduced to a portion of the electrode arrangement. Priming may also be applied in a trolling fashion to cover the entire test region. As it is not known what location is to be most effective, the entire test region is primed.

In a non-limiting example to illustrate the lower intensity of the prime neuromodulation field, one may assume that a patient may feel paresthesia or otherwise perceive the delivery of the neuromodulation field when the neuromodulation current has an amplitude of 10 mA. Thus, 10 mA may be considered to be a perception threshold for the neuromodulation. Therapeutic sub-perception neuromodulation maybe delivered within a range of 30% to 90% of the perception threshold. Thus, in this example, neuromodulation with an amplitude between 3 mA and 9 mA may be therapeutically effective (e.g. provide pain relief). Priming the neural tissue may be accomplished using amplitudes near the lower range of the sub-perception neuromodulation or even below the lower range of the sub-perception neuromodulation such as, by way of example, between 2 mA to 4 mA. The sub-perception neuromodulation affects the neural tissue, but not to the point where the neuromodulation induces the nerve to trigger action potentials. Thus, the prime field may affect the ion concentrations within and outside of the neural pathways responsible for pain relief and/or may affect neurotransmitters responsible for pain relief, such that additional changes by sub-perception neuromodulation may more quickly induce desirable action potentials in these neural pathways responsible for pain relief.

Figures 11A, 11B:
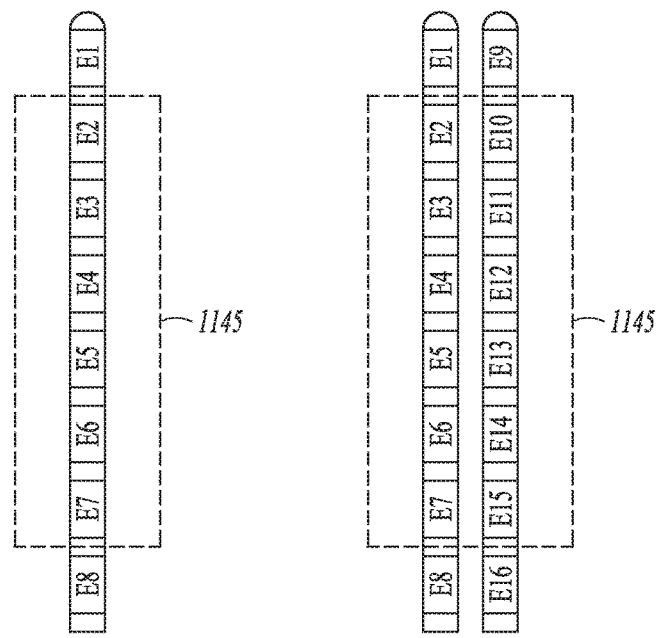
FIGS. 11A-11B illustrate, by way of example and not limitation, electrode arrangements and test regions of neural tissue along the electrode arrangements.

FIGS. 11A-11B illustrate, by way of example and not limitation, electrode arrangements (e.g. E1-E8 in FIG. 11A and E1-E16 in FIG. 11B) and test regions 1145 of neural tissue along the electrode arrangements. These test regions 1145 may extend across the entire electrode arrangement. In some embodiments, the test regions may extend along only a portion of the electrode arrangement. By way of example, some embodiments may allow a user to select the test region and thus select the portion of the electrode arrangement to be tested. In the example illustrated in FIG. 11A the test region is neural tissue along the E2 to E7 electrodes, and in the example illustrated in FIG. 11B the test region is neural tissue along the E2 through E7 and the E10 to E15 electrodes.

Figure 12A:
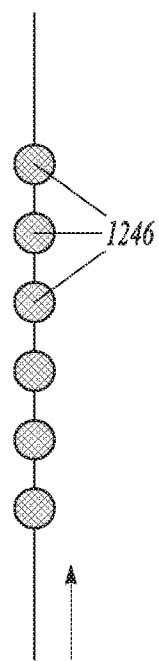
FIGS. 12A-12C illustrate, by way of example and not limitation, neural tissue locations that may be targeted within the test region in one, two and three dimensions, respectively.
Figure 12B:
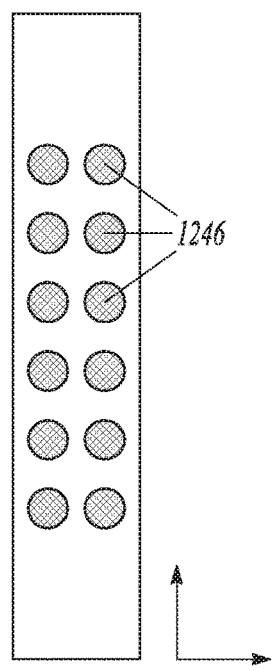
Figure 12C:
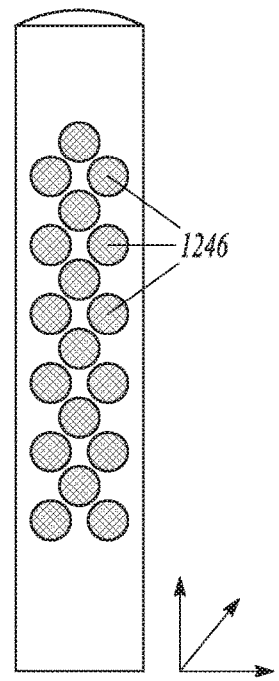

The electrodes in the electrode arrangement may be fractionalized, using different neuromodulation parameter sets, to change the portion of the neural tissue that is modulated. Thus, there may be many neural tissue locations that can be targeted with the test region of neural tissue adjacent to the electrode arrangement. FIGS. 12A-12C illustrate, by way of example and not limitation, neural tissue locations 1246 that may be targeted within the test region in one, two and three dimensions, respectively. In the one-dimensional example illustrated in FIG. 12A, the neural locations that may be targeted may simply be a line of potential targets such as may be observed from a single lead with a linear arrangement of electrodes. In the two dimensional example illustrated in FIG. 12B the neural locations that may be targeted may be considered to lie in a plane proximate to the electrode arrangement. In the three-dimensional example illustrated in FIG. 12C, the neural locations that may be targeted may be considered to be a volume of tissue proximate to the electrode arrangement. By way of example, the two-dimensional and three-dimensional test regions may be implemented using two or more leads of electrodes. Thus, the test regions may be relatively simple or complex shapes, and may include relatively few or relatively many locations to be tested.

Figure 13:
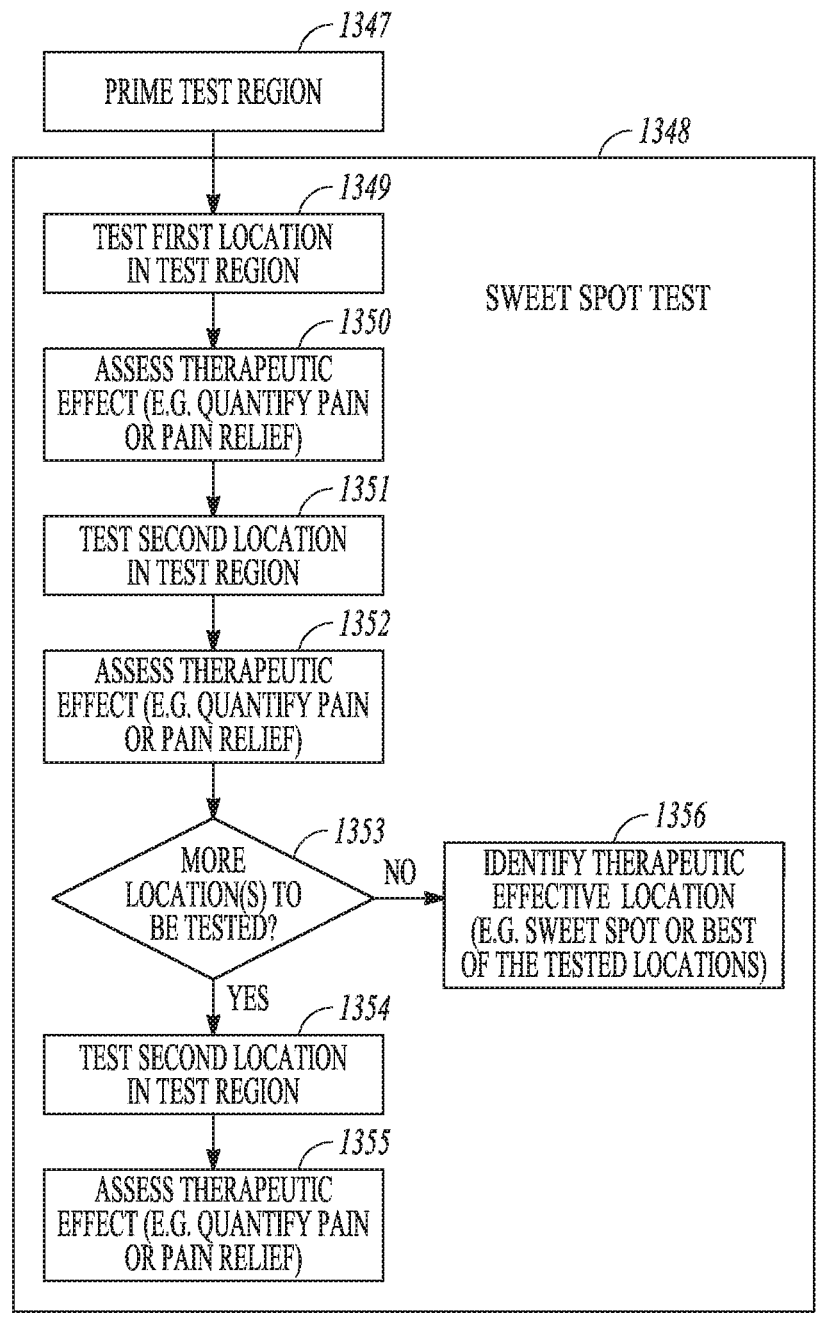
FIG. 13 illustrates an example of a method for finding a sweet spot for sub-perception neuromodulation.

FIG. 13 illustrates an example of a method for finding a sweet spot for sub-perception neuromodulation. In the illustrated example, a test region is primed with the sub-perception neuromodulation field 1347, and the sweet-spot test is performed 1348 to find location of neural tissue that is therapeutically effective when targeted with sub-perception neuromodulation. The sweet spot test may involve a manual process to reprogram the neuromodulation field parameter set with different values to change the targeted location of the neuromodulation field. In some embodiments of the test, the targeted location is automatically changed (e.g. trolled) by automatically changing values of the neuromodulation field parameter set. Some embodiments may semi-automatically change values of the neuromodulation field parameter set to change the targeted location of the neuromodulation field.

At 1349, a first location in the test region is tested by focusing the neuromodulation field onto the first location. At 1350, the therapeutic effect of modulating the first location is assessed. In an example where the therapy is a therapy to alleviate pain, the patient may provide this assessment by quantifying a level of pain or level of pain relief that they are experiencing. In some examples, a biomarker is used to provide an assessment of the therapeutic efficacy of the neuromodulation field focused on the tested location. At 1351, the neuromodulation field parameter set is changed to change the focus of the neuromodulation field to test a second location in the test region. At 1352, the therapeutic effect of modulating the second location is assessed. If more location(s) are to be tested, as illustrated at 1353, the process may continue to 1354 to test the next location and to 1355 to assess the therapeutic effect of the next location. The process may determine or identify the location(s) that are therapeutically effective 1356 by evaluating the quantified effects of the therapy. In some embodiments, the quantified effects may be compared to each other to identify the tested location that has the best therapeutic effect (the sweet spot) or one of the best therapeutic effects (a sweet spot).

The present subject matter may be used to test relatively small locations using a more narrowly focused neuromodulation field such as generally illustrated above in FIGS. 12A-12C, or may be used to test relatively larger locations of neural tissue using a more uniform (less focused) neuromodulation field. The test of larger locations may be followed by a more focused test or tests within one of the larger location. Regardless of whether the test location is relatively large or relatively small, the present subject matter primes the test neural tissue to reduce a wash-in time of the therapy and enable a quick assessment of the effectiveness of the therapy. A few search algorithms are provided below as examples. Other processes for testing locations of neural tissue are possible.

Various embodiments start with full-lead then use a search algorithm to reduce the span and improve energy efficiency. This can be done from the RC or CP, or in the IPG with RC feedback. The proposed algorithms may rely on some form of feedback indicating the effectiveness of the neuromodulation. For example, a patient may provide feedback regarding pain relief. Feedback may also provide a biomarker signal.

The system may include a routine to confirm that the neuromodulation along the full lead is effective and then focus the neuromodulation along a portion of the lead. Thus, for example, a generally uniform neuromodulation field may be provided along this smaller portion of the lead. This field is still broad as it may be provided across an area with multiple electrode contacts, but it is less than the entire electrode arrangement using electrode array(s) on the lead (s).

Various embodiments may provide a rostra-caudal focus routine that includes a binary search routine. The binary search routine segments the lead or array of electrodes from a full set of electrodes into at least two subsets of electrodes that defines partial lead search regions. The binary search routine may confirm that neuromodulation along the full lead is effective.

Figure 14:
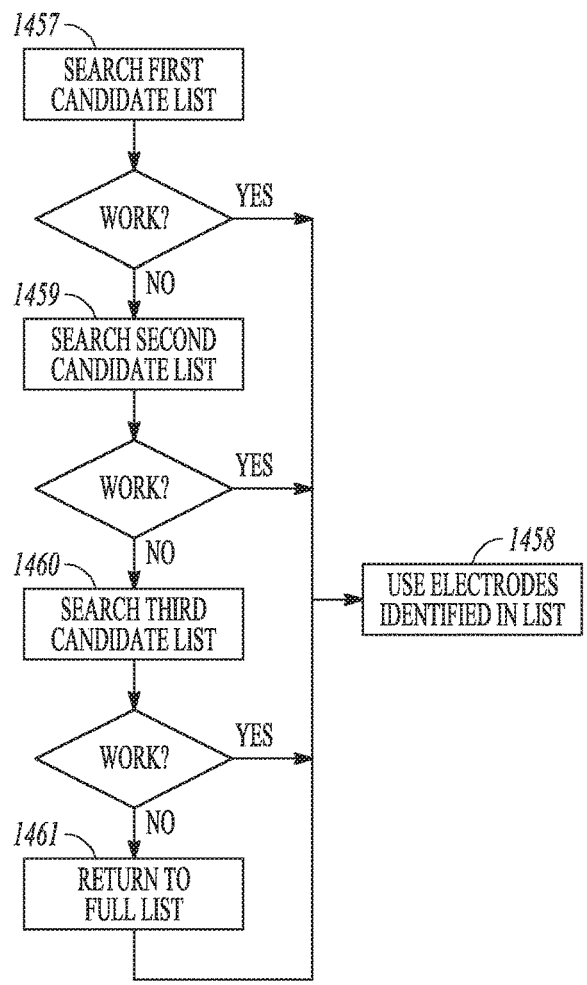
FIG. 14 illustrates, by way of example, aspects of a binary search routine as a rostra-caudal focus routine.

FIG. 14 illustrates, by way of example, aspects of a binary search routine as a rostra-caudal focus routine. A first subset of electrodes that define a first partial lead search region can be tested to determine if the neuromodulation is effective using the first subset 1457. If it is effective, the first subset of electrodes that define the first partial lead search region may be used to deliver the neuromodulation 1458 or for further more focused tests. If it is not effective, then a second subset of electrodes that define a second partial lead search region may be tested to determine if the second subset of electrodes is effective 1459. If it is effective, the second subset of electrodes that define the second partial lead search region may be used to deliver the neuromodulation 1458. If it is not effective, then a third (or nth) subset of electrodes that define a third (or nth) partial lead search region may be tested to determine if the third (or nth) subset of electrodes is effective 1460. If it is effective, the third (or nth) subset of electrodes that define the third (or nth) partial lead search region may be used to deliver the neuromodulation 1458. If it is not effective, then the binary search process may return to the full list of electrodes 1461 which was previously determined to be effective. At least some of the subsets of electrodes may be exclusive of each other. At least some of the subsets of electrodes may intersect with each other. In some embodiments, at least two subsets are exclusive, and at least one subset has an intersection with another subset.

Figure 15:
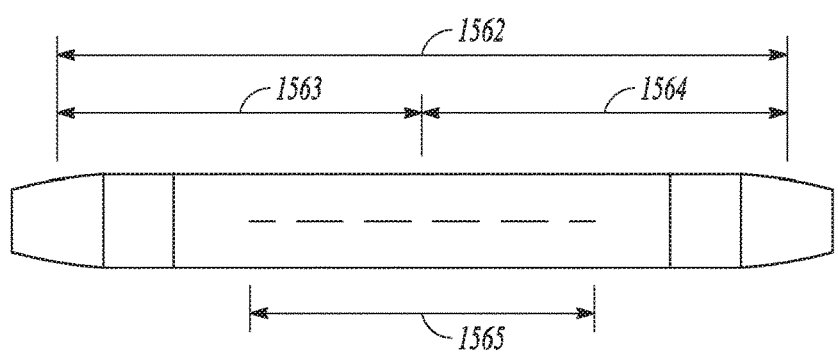
FIG. 15 illustrates an example of the binary search routine.

FIG. 15 illustrates an example of the binary search routine. The lead has a full span 1562 which may be split into three partial lead search regions 1563, 1564 and 1565, each partial search region including a corresponding subset of electrodes. By way of example and not limitation, the first and second subsets 1563 and 1564 of electrodes may be mutually exclusive, and third subset 1565 may include an intersection with the first subset and also may include an intersection with the second set. In an example, the full lead may be bifurcated to provide the first partial lead search region 1563 on a first side of the lead (e.g. left end of electrode array to middle) and the second partial lead search region 1564 on a second side of the lead (e.g. right end of the electrode array to middle). The third partial lead search region 1565 may partially overlap each of the first and second partial lead search regions. Thus, the partial lead search regions may define a first end region, a second end region and a middle region of the lead.

Figure 16A:
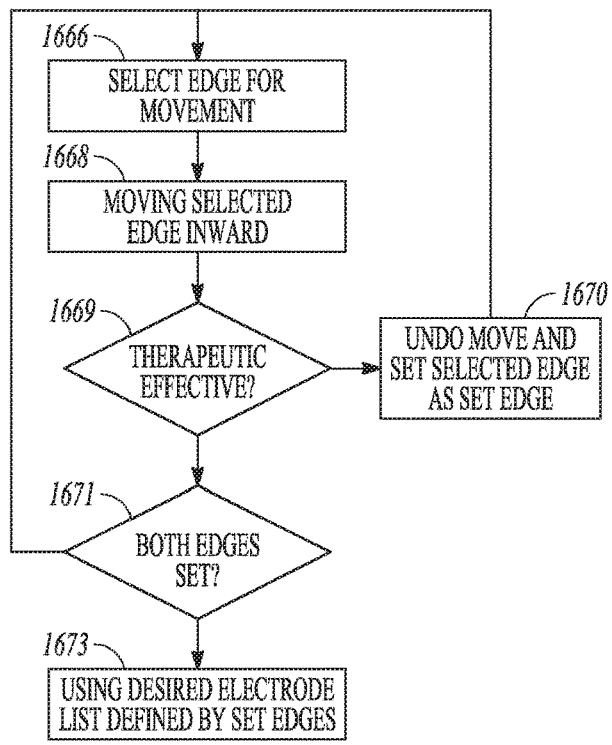
FIGS. 16A-16C illustrate, by way of example, an edge search routine.
Figure 16B:
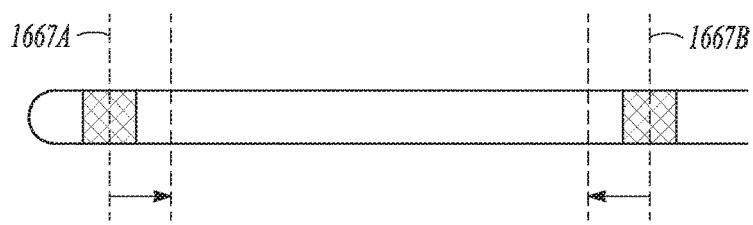
Figure 16C:
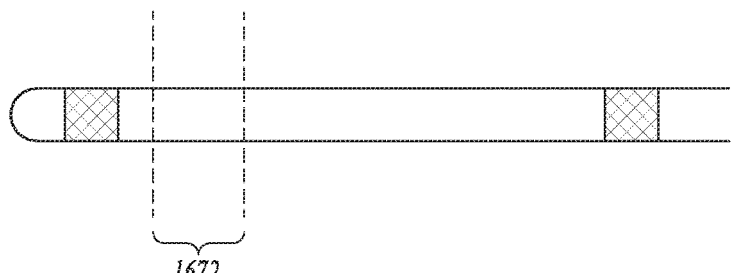

FIGS. 16A-16C illustrate, by way of example, an edge search routine. The edge search routine progressively moves each edge of the active electrodes in the array toward the middle and confirms that the neuromodulation remains effective with the moves. Thus, a first edge can be moved toward the center until the next move toward the center causes the neuromodulation to be ineffective; and a second edge can be moved toward the center until the next move toward the center causes the neuromodulation to be ineffective.

For example, the edge search routine may include selecting an edge of the electrode arrangement (e.g. array) for movement 1666. The selected edge may be one of the two edges 1667A or 1667B illustrated in FIG. 16B. However, there can be more than two edges if more than two regions are being focused. The selected edge is moved inward 1668 toward the other edge for the region of interest. If the reduced set of electrodes is no longer therapeutically effective 1669, then the previous move can be undone and that edge can be set so that is no longer is capable of being selected for movement 1670. The process can return to 1666 to attempt to move the other edge(s). If the reduced set of electrodes continues to be therapeutically effective 1669, then the process returns to 1666 to continue moving edges until such time as all of the edges are set 1671. The final reduced set 1672 of electrodes can be used 1673 to deliver the neuromodulation energy.

According to various embodiments, the programmed system may be configured with a neuromodulation focus routine such as a rostra-caudal focus routine to allow a user to select the desired electrodes for the neuromodulation to be more specific to the desired physiological area. Some embodiments may allow non-contiguous spans to be selected as a result of initial programming and/or neuromodulation refinement later on.

The neuromodulation field may be moved from location to location using an automatic trolling process or through patient control. Candidate trolling algorithms include a monopolar troll (anodic or cathodic) or a bipolar troll or a multipolar troll. The troll can be done with MICC or multiple independent voltage control, or with a timing channel interleaving technique. MICC enables the locus of the neuromodulation to be gradually moved across along the lead or within the array of electrodes. The interleaving of timing channels allows different electrode(s) in different timing channels. Values of stimulation parameter(s) (e.g. amplitude) in the timing channels can be adjusted. Thus by way of example and not limitation, if a monopolar neuromodulation is delivered using a first electrode in a first channel and another monopolar neuromodulation is delivered using a second electrode adjacent to the first electrode in a second channel, then the amplitude of the monopolar neuromodulation in the first channel may be incrementally reduced as the amplitude of the monopolar neuromodulation may be increase in the second channel. In this matter, the locus of the neuromodulation may be gradually adjusted.

Various embodiments troll a neuromodulation field, using an arrangement of electrodes on at least one lead, through neural tissue positions, and perform a quantification procedure multiple times as the neuromodulation field is trolled through the positions. The quantification procedure identifies when the neuromodulation field provides a therapeutic effect (e.g. pain relief). The quantification procedure may include receiving a marking signal that indicates that a neuromodulation intensity achieved the therapeutic effect, and storing a value for the therapeutic effect as well as neuromodulation field parameter data. The neuromodulation intensity may include neuromodulation parameters that affect the patient's perception of the neuromodulation energy. These parameters may include pulse width, rate, amplitude, distribution of current, and electrode polarity (cathode v. anode). By way of example and not limitation, the storage of the parameter data may be in a temporary storage such as but not limited to cache or RAM or in permanent/persistent storage such as but not limited to ROM, a memory device such a hard drive, optical disc, thumb drive, or cloud storage. The quantification process may include receiving a titration signal that indicates an instruction to adjust neuromodulation intensity, and adjusting the neuromodulation intensity in response to receiving the titration signal. The titration signal may be initiated by a patient, or by a clinician or other user who is responding to patient responses.

Figure 17:
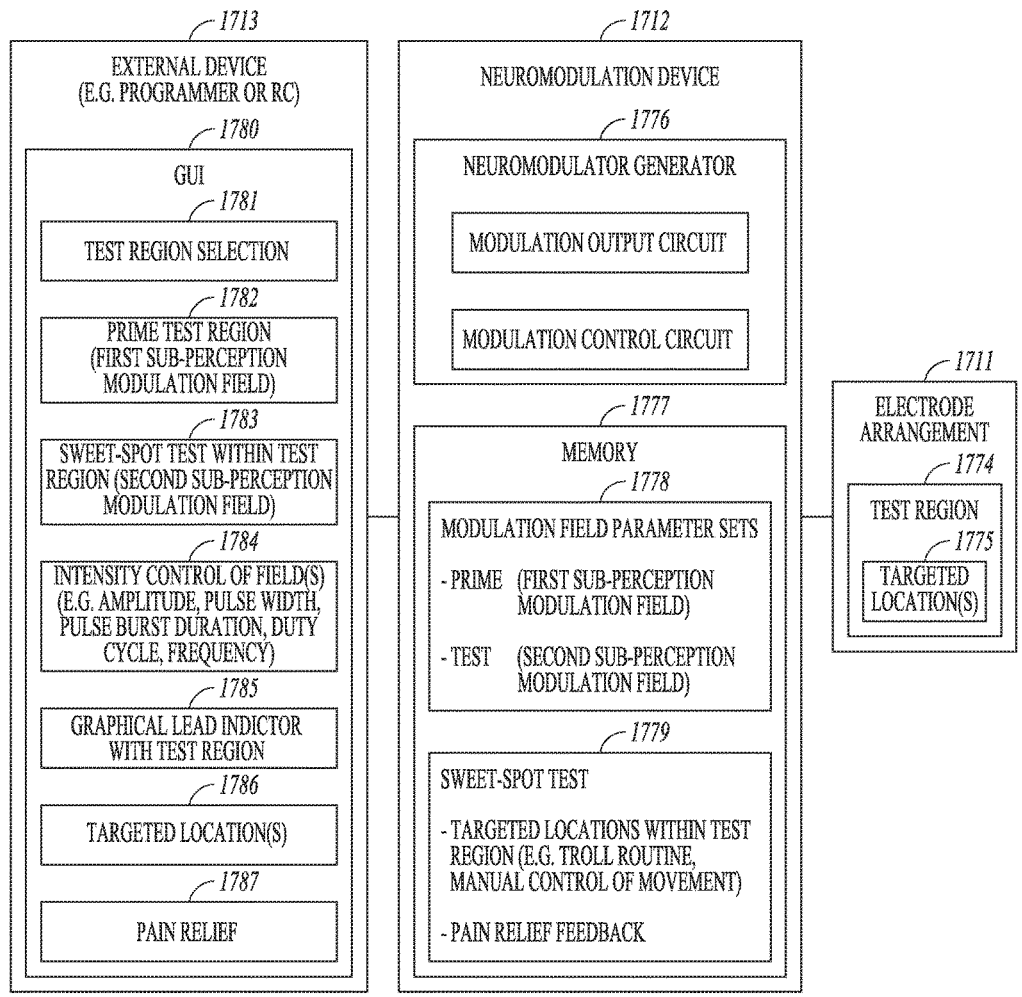
FIG. 17 illustrates an example of a system for finding a sweet-spot for sub-perception neuromodulation.

FIG. 17 illustrates an example of a system for finding a sweet-spot for sub-perception neuromodulation. The system may include an electrode arrangement 1711, a neuromodulation device 1712, and an external device such as a programmer or remote control (RC) 1713. The illustrated electrode arrangement 1711 includes electrodes corresponding to a test region 1774 of neural tissue. The test region is proximate to the electrodes, and may be associated with all electrodes in the electrode arrangement or a subset of the electrodes in the electrode arrangement. The test region 1774 may include targeted location(s) 1775 which may be, as discussed above, a relatively focused small location or a relatively broad location.

The neuromodulation device 1712 may include a neural modulator generator 1776 which may comprise a neuromodulation output circuit and a neuromodulation control circuit such as is generally illustrated in FIG. 3. The neuromodulation device may further include memory 1777, which may include neuromodulation field parameter sets 1778 and a sweet spot test routine 1779. The neuromodulation field parameter sets 1778 may be used by the neuromodulator generator to control the neuromodulation field generated by the electrode arrangement. The neuromodulation field parameter sets may include a first sub-perception neuromodulation field parameter set used by the neuromodulator generator to prime a test region, and include a second sub-perception neuromodulation field parameter set used by the neuromodulator to test location(s) within the test region. The sweet spot test routine 1779 may include instructions for targeting location(s) within the test regions. The instructions for targeting location(s) may include instructions for receiving manual control inputs from a user or may include instructions for performing automated or semi-automated trolling of the movements. The sweet spot test routine 1779 may also include instructions for receiving feedback concerning the effective of the therapy. For example, the instructions may include instructions for receiving a quantification of the therapeutic effect (e.g. a pain rating) from the external device, and associating that quantification with the targeted location.

The external device 1713 may include a graphical user interface (GUI) 1780. Some embodiments of the GUI may provide test region selection element(s) 1781 used to select a test region. Some embodiments may also display the selected test region with respect to the electrode arrangement. Some embodiments of the GUI may include prime neuromodulation element(s) 1782 used to program the first sub-perception neuromodulation field parameter set that controls location and shape of the prime neuromodulation field, and test element(s) 1783 used to program the second sub-perception neuromodulation filed parameter set that controls location and shape of the second neuromodulation field used in performing the sweet spot test. Some embodiments of the GUI may include an intensity control element (s) 1784 configured for use by the user to control the intensity of the first and/or second sub-perception neuromodulation fields. The intensity of the stimulation maybe controlled by controlling an amplitude of the neuromodulation pulses. In addition or as an alternative, the intensity of the stimulation may be controlled by controlling a pulse with of the neuromodulation pulses, the pulse burst duration, the duty cycle of the pulses, the burst on/burst off duty cycle and/or pulse frequency of the neuromodulation pulses. Some GUI embodiments provide an element to provide an indicator 1785 of a graphical lead with a test region identified in relative position with respect to the illustrated lead. Some embodiments may allow the user to set or adjust the test region, such as by dragging illustrated boundaries of the test region on the GUI. Some GUI embodiments provide an element 1786 to provide an indicator of targeted location(s) within a test region, and some embodiments may allow the user to set or adjust the targeted location(s). A GUI example may include element(s) 1787 to allow a user to enter feedback regarding the effective of the therapy. For example, the feedback may be a quantification of pain or pain relief.

In a related embodiment, the GUI embodiments facilitate equivalent display, and control of, the priming fields in addition to the therapeutic fields of the neuromodulation pulses. In an example, the therapeutic and priming signaling are each independently controllable relative to the other. In a related example embodiment, the display of the priming and therapeutic fields is configured to show both in the same spatial reference frame so that the user may make adjustments to the parameters of one while viewing the characteristics of the other.

Figure 18:
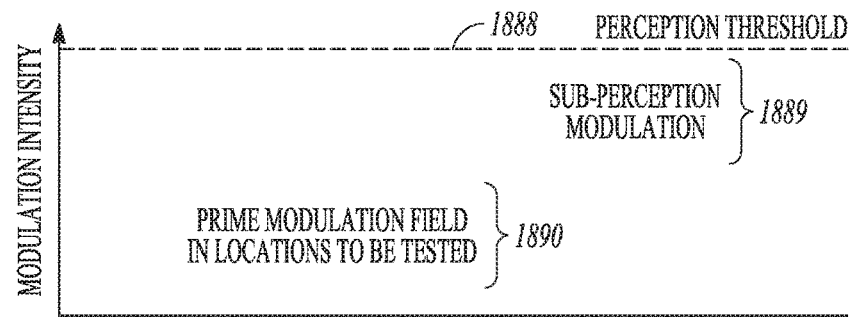
FIG. 18 illustrates, by way of example, and not limitation, sub-perception neuromodulation intensity used to prime the test region and to test a therapeutic effect of locations within the test region.

FIG. 18 illustrates, by way of example, and not limitation, sub-perception neuromodulation intensity used to prime the test region and to test a therapeutic effect of locations within the test region. The perception threshold 1888 illustrates the intensity of the neuromodulation field at the boundary between perceptible neuromodulation and sub-perception neuromodulation. Perceptible neuromodulation is where the neuromodulation field delivers energy that is perceptible to the patient. Examples of perceptible stimulation include stimulation that causes paresthesia. Perceptible neuromodulation may also include neuromodulation that causes a temperature change or a motor response. The therapeutic sub-perception neuromodulation 1889 is therapeutically effective, even though the delivery of the neuromodulation energy is not perceived by the patient. As discussed earlier, the perception threshold may be different for different portions of the electrode arrangement. Some embodiments calibrate the neuromodulation to account for these differences. The prime sub-perception neuromodulation 1890 is generally at a lower energy than the sub-perception neuromodulation 1889.

Figure 19A:
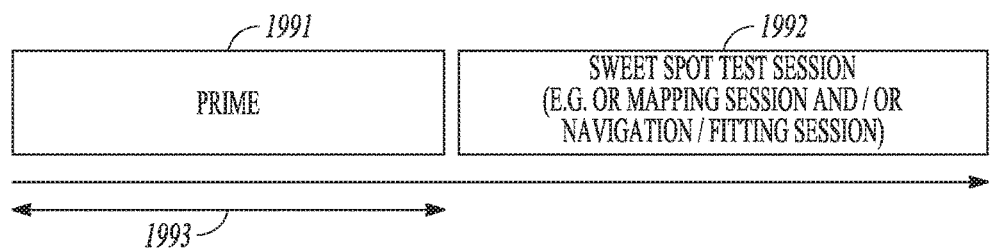
FIGS. 19A-19B illustrate relative timing between the prime neuromodulation field and the sweet spot test session to test a therapeutic effect of locations within the test region.
Figure 19B:
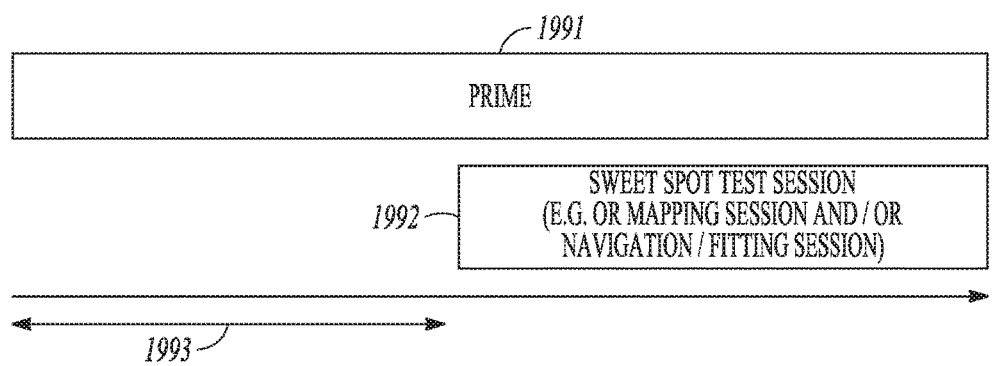

FIGS. 19A-19B illustrate relative timing between the prime neuromodulation field 1991 and the sweet spot test session 1992 to test a therapeutic effect of locations within the test region. In both examples, the prime neuromodulation field 1991 is delivered for a time period 1993 before the sweet spot test session 1992. For example, this time period 1993 may be more than 30 minutes. In some embodiments, this time period 1993 is more than an hour. In some embodiments the time period 1993 is more than 6 hours and less than a week. In some embodiments, the time period 1993 is longer than 1 day and shorter than 3 days. In the embodiment illustrated in FIG. 19A, the prime neuromodulation field 1991 is stopped before the sweet spot test session 1992 begins. There may be a time period 1994 between the prime neuromodulation field and the sweet spot test session without any neuromodulation. In some embodiments, the prime-neuromodulation field continues during at least a portion of the sweet spot test session. FIG. 19B illustrates an example in which the sweet spot test session 1992 is performed while the prime neuromodulation field 1991 is generated. The sweet spot test session may be performed during an operation room mapping session and/or during a navigation fitting session.

Figure 20:
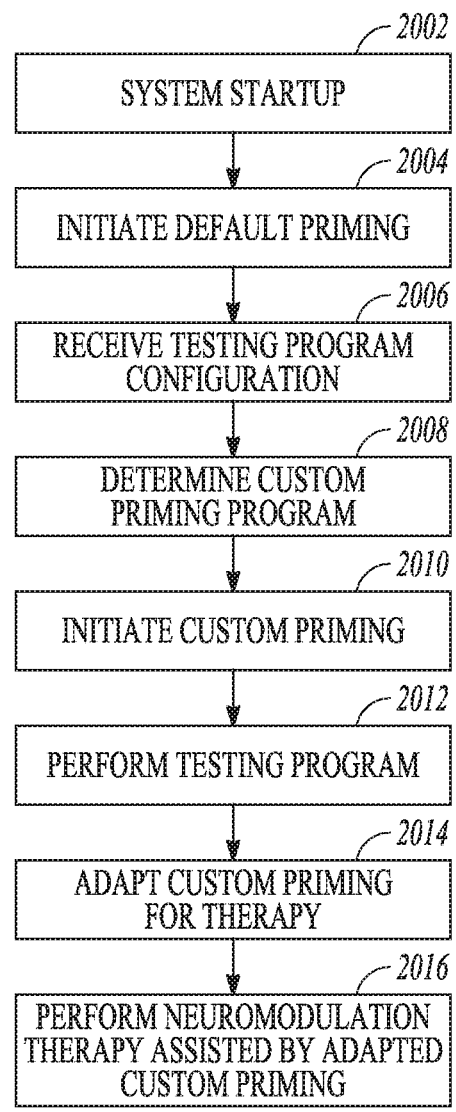
FIG. 20 is a flow diagram illustrating an example of a process of operating a neuromodulation system from startup, according to some embodiments.

FIG. 20 is a flow diagram illustrating an example of a process of operating a system for setting neuromodulation field-generating parameters for sub-perception neuromodulation, such as the neuromodulation device 1712 depicted in FIG. 17, from system startup, according to some embodiments. At 2002, the device performs startup operations, including such activities as a self-test, and an in-situ electrical test. In response to successful completion of the self-test, and the in-situ electrical measurements are carried out. The in-situ electrical measurements may include such measurements as determining the connection to an electrode arrangement, and measuring impedance across various pairs of electrodes to ascertain placement of the electrodes at the target region of the patient, for instance. To this end, the impedance measurement may be compared against a predefined range of acceptable impedance values to assess proper placement of the electrode arrangement.

In response to a determination that the device is operational, and placed in an operative configuration with respect to a test region of the patient, a default priming program is initiated at 2004. The default priming program may be preconfigured in the memory 1777 as part of the neuromodulation field parameter sets 1778, for example. In a related embodiment, the default priming program is initiated independently of any user-originated instructions.

For example, the in-situ measurements may include a determination of the type of electrode arrangement, which in turn, may be indicative of the type of neuromodulation for which the neuromodulation device 1712 is to be configured. The device's memory 1777 may contain multiple sets of priming program parameter values for the default priming program, such as pulse amplitude, pulse duration, pulse repetition rate, pulse waveform, periodicity for groups of pulses (where applicable), and electrode selections for spatially defining the priming field. The neuromodulation device 1712 may select a suitable default priming program from the available options based on a predefined set of selection criteria, e.g., in the form of a lookup table or program logic.

In a related embodiment, the default priming program is configured to apply a spatially broadly-distributed priming field to the region at which the electrode arrangement is placed.

In an example embodiment, the default priming program configures the neuromodulation device 1712 to apply the default priming signaling to be started immediately and continue indefinitely, or until a further configuration instruction is provided. In a related embodiment, a time limit, such as 30 days, may be enforced, after which the default priming program may stop automatically. In another related embodiment, the default priming program includes a delayed start time, which may be preconfigured at the time of implantation or initial setup of the neuromodulation device 1712. For example, if, at the time of system configuration, a healthcare provider knows that the patient has an appointment to return to the clinic for sweet-spot testing in seven days, the start time for the default priming may be set to begin the default priming two or three days in advance of the appointment.

At 2006, the neuromodulation device 1712 receives testing program configuration instructions. As an example, the testing program configuration instructions may include information for configuring the neuromodulation device 1712 as part of the sweet-spot testing and configuration. The testing program configuration instructions may specify parameters such as the type of planned neuromodulation therapy, target tissue of the sweet-spot testing (which may be based on all available electrodes of the electrode arrangement, or some subset thereof), and signal characteristics (e.g., waveform parameters, pulse amplitude, pulse duration, pulse repetition frequency, periodicity of pulse groupings, parameter variability, etc.). The testing program configuration instructions may be indicative of the neuromodulation objective, such as whether the target region is in the dorsal column or the brain. Similarly, the ascertained neuromodulation objective may be whether the neuromodulation is to stimulate the target neural tissue, or whether it is to inhibit stimulation, for example. This information may be explicitly indicated in the testing program configuration instructions, or it may be inferred based on the waveform parameters, for example. The testing program configuration instructions may be loaded into the neuromodulation device 1712 before or after system startup according to various use cases.

At 2008, in response to the testing program configuration instructions, the neuromodulation device 1712 determines a custom priming program. The custom priming program is adapted to enhance the effectiveness of the testing program. For example, if the neuromodulation objective is to stimulate the target tissue, the custom priming program may be adapted to enhance sensitivity to the neuromodulation treatment signal. In general, the custom priming program will supersede the default priming program. In the particular case where the testing program configuration instructions are received before initiation of the default priming program, the custom priming program may entirely replace the default priming program.

Figure 21:
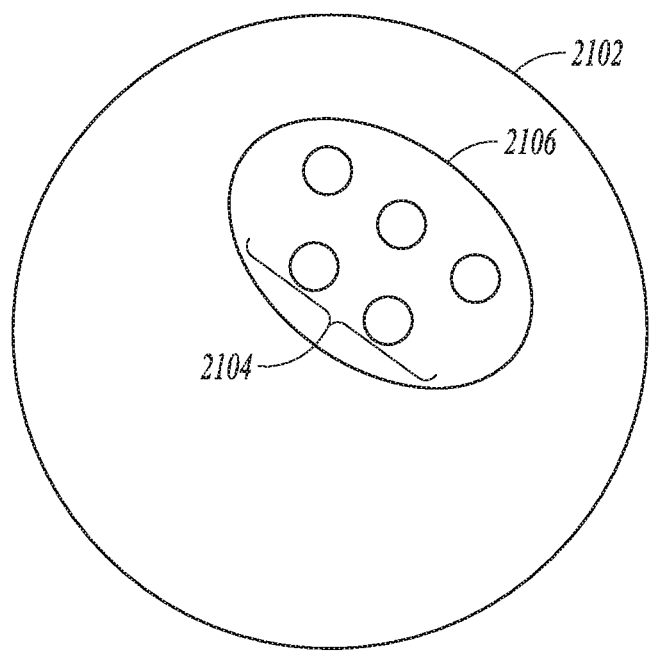
FIG. 21 is a simplified Venn diagram illustrating examples of the relative sizes and locations of a default priming field, a set of testing program fields and a custom priming field according to an embodiment.

In a related embodiment, the custom priming program is adapted to produce a priming field having specific spatial correspondence to the field(s) to be produced by the testing program. FIG. 21 is a simplified Venn diagram illustrating examples of the relative sizes and locations of the default priming field 2102 of the default priming program, the testing program fields 2104, and the custom priming field 2106. In the example depicted, the testing program fields 2106 collectively represent a subset of the default priming field. The custom priming field 2106 covers the testing program fields 2104, but is itself a subset of the default priming field 2102. Reducing the default priming field to the smaller size of the custom priming field 2106 effectively primes the target tissue for the testing program fields 2104, but provides some energy savings compared with the default priming field 2102.

In an embodiment, the custom priming program is determined by local processing operations performed by the neuromodulation device 1712. This may be accomplished by application of decision criteria stored in memory 1777. The decision criteria may take any suitable form or algorithm, such as lookup table, support vector machine, nearest-neighbor classifier, if-then (or equivalent) logic, or the like. In another embodiment, the neuromodulation device 1712 determines the custom priming program by obtaining the custom priming program from a remote device, such as external device 1713, which computes the custom priming program and transfers it to the neuromodulation device 1712.

At 2010, the neuromodulation device 1712 initiates the custom priming operations according to the custom priming program. At 2012, the testing program is performed. As described above, the testing program may include sweet-spot testing, field intensity, therapy parameter determination, and the like. In various embodiments, the custom priming may be carried out during the testing program. In a related embodiment, the custom priming may be time-interleaved with the testing program such that neuromodulation pulses and the priming pulses do not coincide for the same target tissue. In one such example, a blanking period may be defined that ensures some time period before and after each neuromodulation pulse when the priming signaling is prohibited. Depending on the configuration of the neuromodulation device and on the electrode arrangement, priming pulses may be applied to regions that are spatially separate from the target tissue to which a focused therapy pulse is applied, contemporaneously with the therapy pulse.

At 2014, based on the results of the testing program, such as the sweet-spot selections, the selected neuromodulation therapy signal parameters, etc., the custom priming therapy is adapted to support the neuromodulation therapy to be administered. The adaptation of the custom priming therapy may be accomplished using similar methodology to determining the custom priming at 2008, though in some embodiments adaptation of the custom priming involves primarily limiting the custom priming to certain subsets of the original custom priming parameters. For example, the priming field may be further focused onto target tissue that are targeted by the selected therapy sweet-spot(s).

The signal parameters of the adapted custom priming may also be adjusted to more closely correspond to the specific selected therapeutic neuromodulation signaling. For instance, the adapted custom priming may be optimized for enhancing sensitivity to the therapy signals. In a related embodiment, the adaptation of the custom priming is performed during the testing program, concurrently with operation 2012. In one such embodiment, the adapted custom priming and the neuromodulation therapy signaling are varied and refined during the testing program together to produce a combination of priming and therapy that are collectively optimized for energy efficiency (without necessarily compromising on therapeutic effectiveness) so that the battery life of the device, particularly in the case of an implantable device, man be maximized. For example, the amplitude or duty cycle of the more-energetic therapeutic pulses may be reduced with the addition of the less-energetic priming pulses. This approach may be practical provided that the total energy expended by the added priming pulses is less than the energy savings of the reduced therapeutic pulses, and provided that the therapeutic effectiveness under the combined arrangement is sufficient to meet the needs of the patient.

Adaptation of the custom priming for therapy may be performed by the neuromodulation device 1712, or by a remote device, such as external device 1713, which may compute the custom priming program adaptation and transfer it to the neuromodulation device 1712.

Figure 22A:
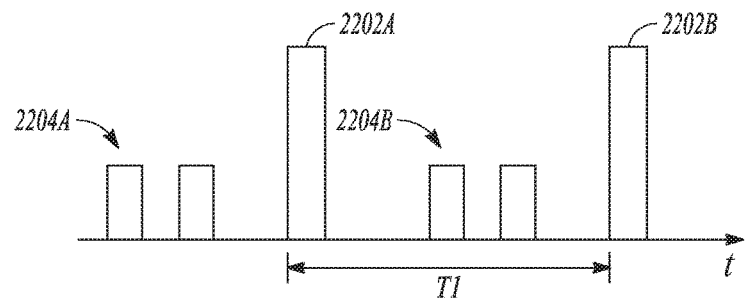
FIGS. 22A-22C illustrate examples of a neuromodulation device performing neuromodulation therapy assisted by adapted custom priming according to some embodiments.
Figure 22B:
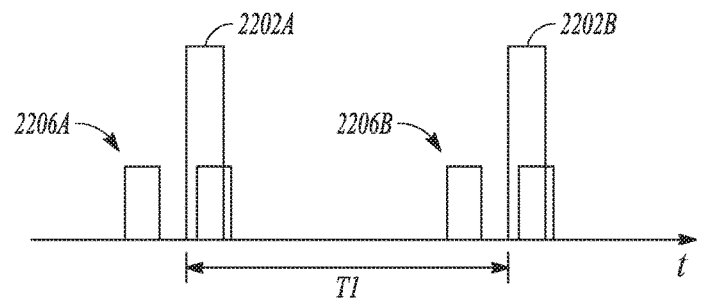
Figure 22C:
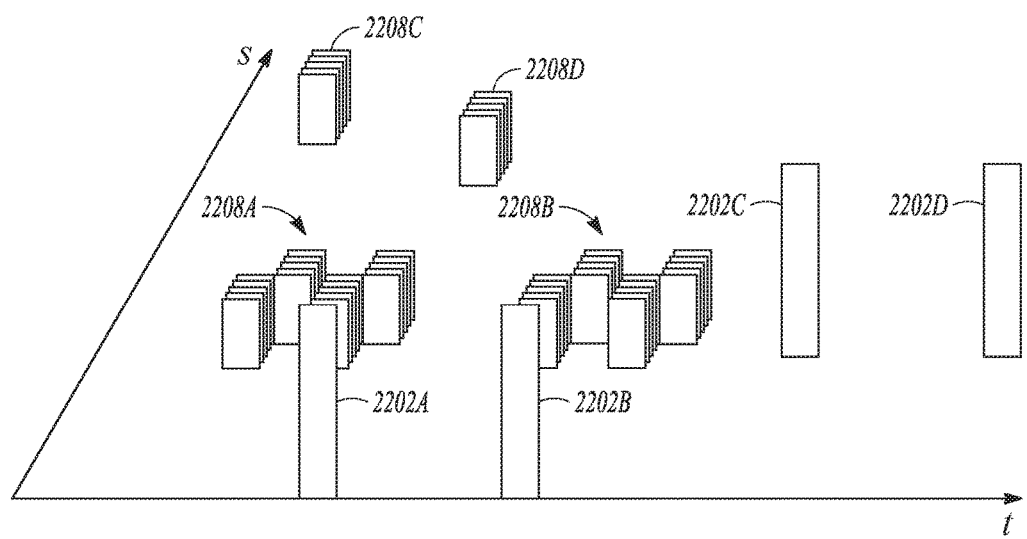

At 2016, the neuromodulation device performs neuromodulation therapy assisted by adapted custom priming according to some embodiments. The operation of one such embodiment is illustrated in FIGS. 22A-22C. In FIG. 22A, therapeutic neuromodulation pulses 2202A and 2202B are administered at a period T1. Bursts of priming pulses 2204A and 2204B are interspersed with therapeutic pulses 2202A and 2202B without temporal overlap of pulses. FIG. 22B illustrates another mode of operation, where bursts of priming pulses 2206A and 2206B overlapping with therapeutic pulses 2202A and 2202B.

In various embodiments, the priming pulses may be spatially distinct from the therapy pulses. For instance, in FIG. 22C, an additional axis s, representing the spatial positioning of the fields produced by the priming and therapeutic pulses, is shown. The s axis in this example is a one-dimensional oversimplification of the spatial positioning As depicted, therapeutic pulses 2202A and 2202B are successively administered at the same location (i.e., their fields targeting the same tissue). The fields generated by therapeutic pulses 2202C and 2202D are located at a different location. In this example, priming pulses 2208A and 2208B, each of which produces a field that occupies more space than the more localized therapeutic pulses 2202, precede therapeutic pulse 2202C, which represents the start of therapeutic pulse application at a new location.

This example operation supports an embodiment in which the neuromodulation device cycles its application of neuromodulation therapy among a plurality of electrotherapy administration vectors, each of which has been demonstrated to produce a sufficient therapeutic effectiveness for the patient. Cycling of administration vector may, in some cases, help to manage habituation, or the building-up of tolerance to the therapy by the patient from repeated exposure at the same treatment site. The priming pulses 2208 preceding the therapeutic pulses 2202C and 2202D at the new location may be applied for hours or days prior to the electrotherapy location change to sensitize the new location.

In a related embodiment, as depicted, additional priming pulses 2208C and 2208D are administered at various other locations. Notably, these priming pulses are less intensive than groups of priming pulses 2208A and 2208B because the neuromodulation device is not expecting to administer treatment pulses in the locations of priming pulses 2208C and 2208D. Instead, priming pulses 2208C and 2208D are administered to mildly sensitize their respective locations in anticipation of future therapeutic pulse administration at those locations.

The examples depicted in FIGS. 22A-22C demonstrate that, according to various embodiments, the priming and therapeutic stimulation signals may be temporally coordinated to improve the effectiveness of the therapy. They may be overlapping, partially overlapping, or non-overlapping. In addition, the priming and therapeutic signals may be interleaved.

In related embodiments, the priming and therapeutic stimulation signals may be spatially coordinated. Their respective fields may have the same, or different, application vectors. In the case of there being different spatial characteristics, in one type of embodiment, the priming signaling may have a wider spatial presence, while the therapeutic signaling may be relatively more focused.

Figure 23:
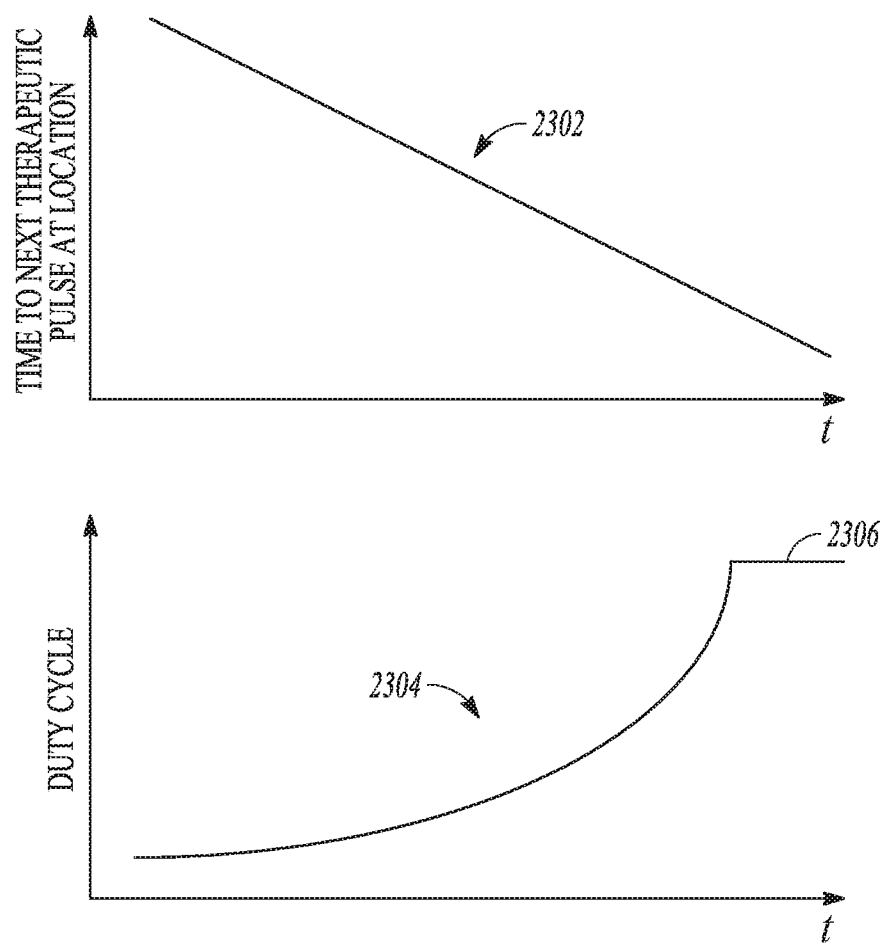
FIG. 23 is a diagram illustrating administration of priming signaling using variable energy according to some embodiments.

FIG. 23 is a diagram illustrating administration of priming signaling using variable energy according to some embodiments. Two curves are depicted along a common time axis, t. Curve 2302 in the top graph represents the time until the next therapeutic pulse at a given location. Curve 2304 in the bottom graph represents the duty cycle for priming pulses at the same location, in the time leading up to the next therapeutic pulse. The graph indicates a trend, rather than individual duty cycle values of discrete pulses, though in practice, the latter would be implemented in the realization of this embodiment. As depicted, the duty cycle increases until a maximum value is reached at 2306. In this embodiment, the duty cycle represents a variable amount of energy applied via the priming pulses. This embodiment is intended to intensify the priming as the next therapeutic pulse approaches. To save energy over time, after the application of the therapeutic pulse, the duty cycle drops back down to its initial value. It will be understood that the therapeutic pulse, in its own right, provides a priming effect; thus, the priming pulses may not add any further benefit in the time immediately following a therapeutic pulse.

In a related embodiment, the efficacy of the priming signaling is electrically measured by the neuromodulation device. In one example, local field potential (LFP) is measured during, or immediately after, administration of priming. In another example, electrically-evoked compound action potential (eCAPS) is measured. In another related embodiment, contact impedance before and after priming is measured. These measurements may be utilized in a feedback control system that adjusts one or more parameters of the priming signaling, such as amplitude, duty cycle, etc., based on a measured quantity indicative of the effectiveness of the priming.

Figure 24:
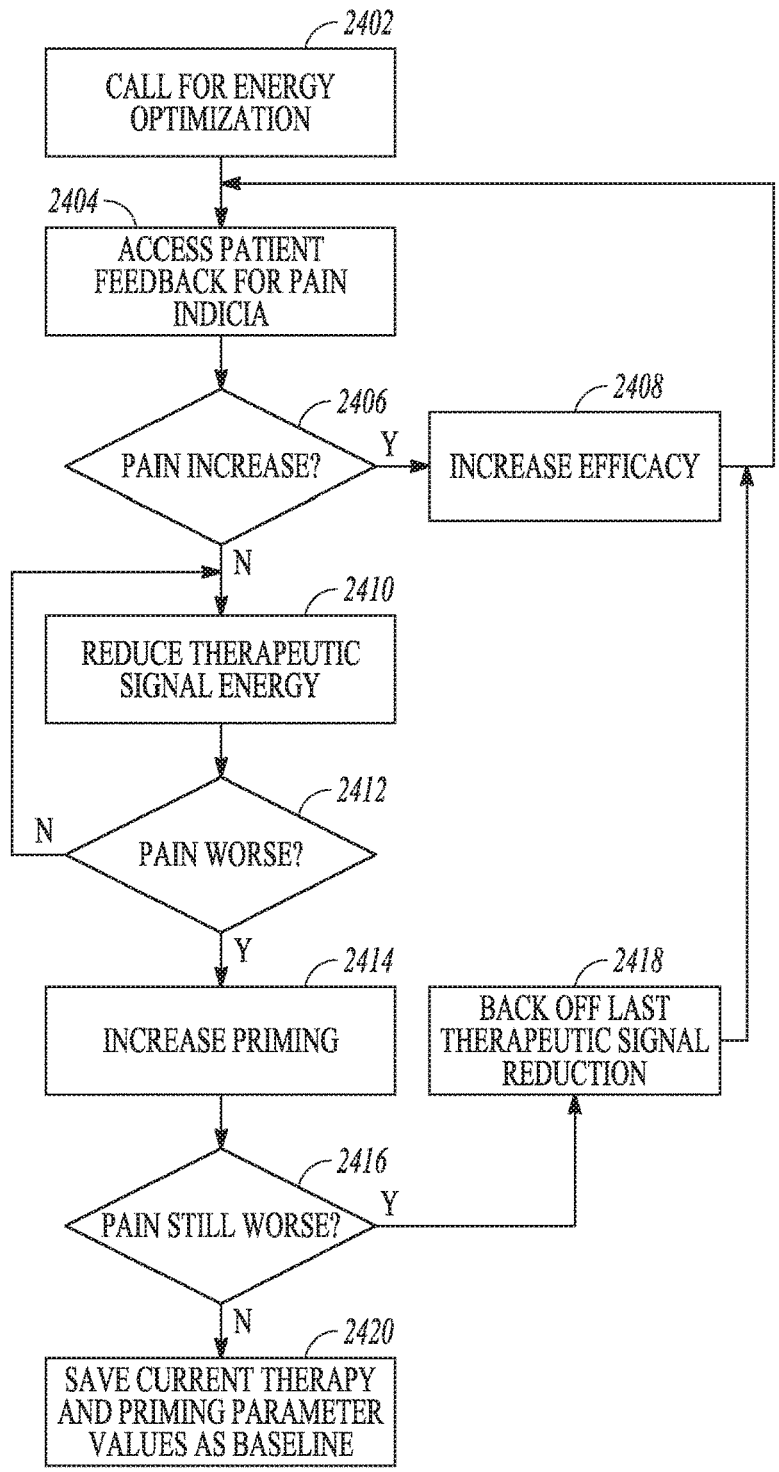
FIGS. 24-25 are flow diagrams illustrating examples of energy-optimization processes incorporating the use of priming in conjunction with therapy signaling according to various embodiments.

In a related embodiment, priming and therapy signaling are varied in coordinated fashion during testing, during therapy, or at both times, to optimize a performance measure, such as energy-efficiency. FIG. 24 is a flow diagram illustrating an example of an energy-optimization process according to an embodiment. According to various embodiments, the process may be carried out by a neuromodulation device, such as neuromodulation device 1712, utilizing patient feedback via external device 1713, for example. The process begins at 2402 in response to a call for energy optimization. The call may occur in response to a passage of time, in response to an event, or some combination of the two. At 2404, the neuromodulation device accesses patient feedback to ascertain if the patient is reporting any indicia of pain or discomfort. The patient feedback may be obtained via external device 1713, or it may be obtained through detection of movement or speech by neuromodulation device 1712.

Decision 2406 determines if the patient reported pain or discomfort and, in the affirmative case, the process advances to 2408 to increase the efficacy of the neuromodulation signaling. Any number of steps may be taken to increase the efficacy according to various embodiments. For instance, the amplitude, duty cycle, or other parameter of the therapy signal may be increased to add energy in the therapeutic signaling. The waveform may be adjusted, or the administration vector may be changed to stimulate different target tissue. Appropriate changes may also be made to the priming signaling. The process then loops back to 2404 to re-assess the patient's condition.

If decision 2406 determines that the patient is not reporting pain or discomfort, then the process advances to 2410, where the energy of the therapeutic signal is incrementally reduced. This may be achieved, for example, by reducing the duty cycle, amplitude, or other parameter(s). Block 2412 checks if the patient reports any worsening of the pain or discomfort. In the negative case, the process loops back to block 2410 to make a further incremental reduction of therapeutic signal energy. In the affirmative case, the priming is increased at 2414. Here, the priming may help to sensitize the target tissue to the lower-energy therapeutic signal to increase the therapy effectiveness. Notably the increase in priming energy expenditure is much smaller than the incremental reduction of the therapeutic signal's energy.

The process advances to decision 2416, where the patient's feedback is checked again to see if the pain or discomfort is still at an unacceptable level. In the case where the patient is satisfied with the reduced level of therapy, the current therapy and priming parameter values are saved as the baseline values at 2420 to be used going forward. However, if at decision block 2416 the patient reports an unacceptable level of pain, then the most recent therapeutic signal reduction is backed off at 2418, and the process loops back to block 2404 to access the patient's feedback.

Figure 25:
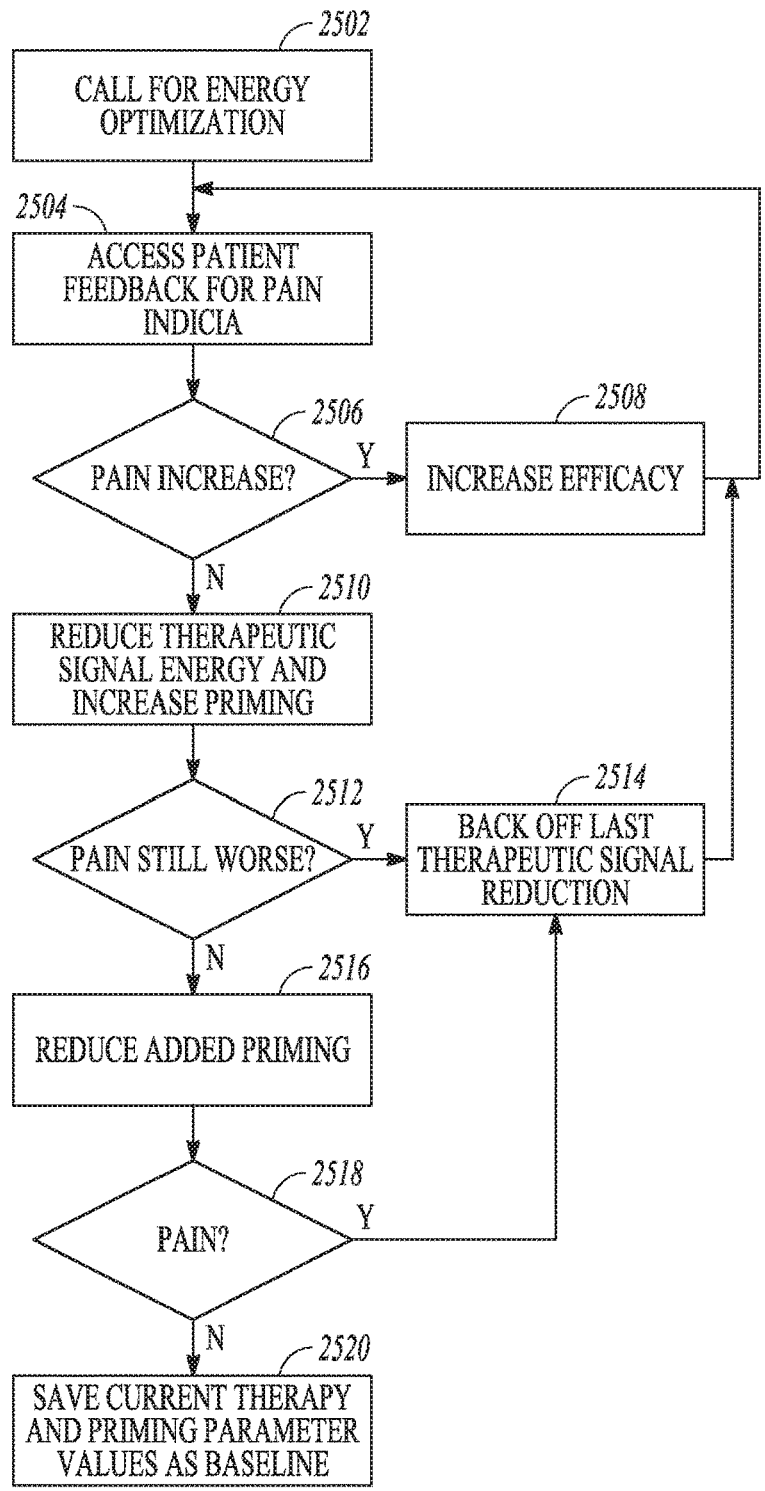

FIG. 25 is a flow diagram illustrating another example of an energy-optimization process according to a related embodiment. At 2502 a call for energy optimization is received. At 2504, the neuromodulation device accesses patient feedback to ascertain if the patient is reporting any indicia of pain or discomfort, which may be obtained in similar fashion as described above with reference to FIG. 24. Decision 2506 determines if the patient reported an increase pain or discomfort and, in the affirmative case, the process advances to 2508 to increase the efficacy of the neuromodulation signaling. Any number of steps may be taken to increase the efficacy according to various embodiments. For instance, the amplitude, duty cycle, or other parameter of the therapy signal may be increased to add energy in the therapeutic signaling. The waveform may be adjusted, or the administration vector may be changed to stimulate different target tissue. Appropriate changes may also be made to the priming signaling. The process then loops back to 2504 to re-assess the patient's condition.

If decision 2506 determines that the patient is not reporting pain or discomfort, then the process advances to 2510, where the energy of the therapeutic signal is incrementally reduced. This may be achieved, for example, by reducing the duty cycle, amplitude, or other parameter(s). In the embodiment depicted, the priming energy is increased at this stage to assist the therapeutic signaling; however, the overall result is a net reduction in energy expenditure. Block 2512 checks if the patient reports any pain or discomfort and, if this is the case, then the reduction is reversed to restore the prior state of the signaling at 2514.

Otherwise, if the energy reduction is successful, i.e., the patient does not report an increase in pain or discomfort, then the process advances to 2516, where the added priming energy is removed in an effort to realize further energy savings. Decision 2518 checks for patient pain or discomfort following this further energy reduction. In the case where the patient is satisfied with the reduced level of therapy, the current therapy and priming parameter values are saved as the baseline values to be used at 2520. Notably, operations 2510-2518 utilize priming as a way to more gradually reduce the total energy expenditure, thereby reducing the likelihood that the system causes the patient some discomfort in its work to achieve energy savings.

In a related embodiment, the system facilitates a control for the patient or healthcare provider to indicate pain or discomfort at any time. In response, the neuromodulation device may increase the efficacy of therapy. In one example, the increase in efficacy is performed with significantly larger increments than reductions in energy expenditure to provide faster symptom relief for the patient. The process of FIG. 25 may then be called in response to the increase in efficacy to gradually incrementally reduce the energy expenditure to a level that maintains effective treatment.

In addition to the Examples discussed in the Summary Section above, some other non-limiting examples are provided as follows.

Example 21 is directed to a system for configuring a neuromodulation device, the system comprising: means for receiving testing program configuration instructions including therapeutic neuromodulation field-setting parameters; means for determining a custom priming program in response to the testing program configuration instructions, wherein the custom priming program controls the neuromodulation device to generate a priming field with specific correspondence to the therapeutic neuromodulation field to be produced by the testing program; means for executing the custom priming program to generate a priming field to produce a priming effect in priming-targeted neural tissue, wherein the priming effect causes a change in sensitization of the priming-targeted neural tissue to a therapeutic neuromodulation field; and means for executing the testing program to generate the therapeutic neuromodulation field to produce a therapeutic effect in therapy-targeted neural tissue.

In Example 22, the subject matter of Example 21 optionally includes wherein the priming program is initiated prior to execution of the testing program.

In Example 23, the subject matter of any one or more of Examples 21-22 optionally include wherein the therapeutic neuromodulation field-setting parameters define a plurality of therapeutic neuromodulation field locations in the therapy-targeted neural tissue, and wherein the custom priming program is adapted to cause the neuromodulation device to produce at least one priming field having specific spatial correspondence to the plurality of therapeutic neuromodulation field locations.

In Example 24, the subject matter of any one or more of Examples 21-23 optionally include means for adapting the custom priming program, by the neuromodulation device, in response to a result of execution of the testing program to focus the custom priming program on a selected set of the therapeutic neuromodulation field-setting parameters determined to be most effective by execution of the testing program.

In Example 25, the subject matter of any one or more of Examples 21-24 optionally include wherein parameters of the custom priming program are determined by the neuromodulation device by application of predefined decision criteria stored locally on the neuromodulation device.

In Example 26, the subject matter of any one or more of Examples 21-25 optionally include wherein the custom priming program is determined by the neuromodulation device based on receiving the custom priming program from a remote device.

In Example 27, the subject matter of any one or more of Examples 21-26 optionally include wherein the custom priming program is executed during execution of the testing program.

In Example 28, the subject matter of Example 27 optionally includes wherein the testing program defines a plurality of distinct therapeutic neuromodulation field locations in the therapy-targeted neural tissue to be targeted at corresponding different times, including a first location and a second location; and wherein the custom priming program is to cause the neuromodulation device to direct the priming field to the second location during application of the therapeutic neuromodulation field to the first location.

In Example 29, the subject matter of any one or more of Examples 27-28 optionally include wherein the neuromodulation device is configured to determine the custom priming program based on the testing program such that the priming field is generated in temporal relationship with the therapeutic neuromodulation field.

In Example 30, the subject matter of Example 29 optionally includes wherein the temporal relationship is varied during execution of the testing program and custom priming program to determine a minimal energy expenditure of the neuromodulation signaling.

The above detailed description is intended to be illustrative, and not restrictive. The scope of the disclosure should, therefore, be determined with references to the appended claims, along with the full scope of equivalents to which such claims are entitled.

What is claimed is:
1. A neuromodulation system, comprising:
neuromodulation generator circuitry configured to use electrodes of an electrode arrangement to generate neuromodulation fields including:
a therapeutic neuromodulation field to produce a therapeutic effect in therapy-targeted neural tissue; and
a priming field to produce a priming effect in priming-targeted neural tissue, wherein the priming effect causes a change in sensitization of the priming-targeted neural tissue to the therapeutic neuromodulation field; and
a controller configured to initiate a default priming program, to receive testing program configuration instructions including therapeutic neuromodulation field-setting parameters for a testing program, and to determine a custom priming program to replace the default priming program in response to the testing program configuration instructions, wherein the default priming program controls the neuromodulation generator circuitry to generate the priming field as a default priming field distributed in a region where the electrode arrangement is placed, the custom priming program controls the neuromodulation generator circuitry to generate the priming field as a custom priming field with specific correspondence to the therapeutic neuro- modulation field to be produced by the testing program, and the custom priming field is a subset of the default priming field.

2. The system of claim 1, wherein the controller is configured to initiate the custom priming program prior to execution of the testing program.

3. The system of claim 1, wherein the therapeutic neuromodulation field-setting parameters define a plurality of therapeutic neuromodulation field locations in the therapy-targeted neural tissue, and wherein the custom priming program is adapted to cause the neuromodulation generator circuitry to produce at least one priming field having specific spatial correspondence to the plurality of therapeutic neuromodulation field locations.

4. The system of claim 1, wherein the controller is further configured to adapt the custom priming program in response to a result of execution of the testing program to focus the custom priming program on a set of the therapeutic neuromodulation field-setting parameters selected based on therapeutic effectiveness of the testing program.

5. The system of claim 1, further comprising a neuromodulation device including the neuromodulation generator circuitry, the controller, and a memory accessible by the controller, and wherein the custom priming program is determined by local processing operations performed by the controller by application of predefined decision criteria stored locally on the memory.

6. The system of claim 1, wherein the controller is configured to receive the custom priming program from a remote device.

7. The system of claim 1, wherein the controller is configured to execute the custom priming program to generate the priming field during execution of the testing program.

8. The system of claim 7, wherein the testing program defines a plurality of distinct therapeutic neuromodulation field locations in the therapy-targeted neural tissue to be targeted at corresponding different times, including a first location and a second location, and the custom priming program is to cause the neuromodulation generator circuitry to direct the priming field to the second location during application of the therapeutic neuromodulation field to the first location.

9. The system of claim 7, wherein the controller is configured to determine the custom priming program based on the testing program such that the priming field is generated in temporal relationship with the therapeutic neuromodulation field.

10. The system of claim 9, wherein the temporal relationship is varied during execution of the testing program and custom priming program to determine a minimal energy expenditure of the neuromodulation signaling.

11. The system of claim 1, wherein the therapeutic neuromodulation field to be produced by the testing program is a subset of the custom priming field.

12. The system of claim 1, wherein the controller is configured to control the neuromodulation generator circuitry to generate the therapeutic neuromodulation field and the priming field in a time-interleaved manner.

13. The system of claim 1, comprising a neuromodulation device including the neuromodulation generator circuitry and the controller.

14. The system of claim 13, wherein the neuromodulation generator circuitry is configured to generate the therapeutic neuromodulation field by delivering therapeutic neuromodulation pulses using the electrode arrangement and to generate the priming field by generating priming pulses using the electrode arrangement.

15. The system of claim 13, wherein the neuromodulation device further comprises a memory, and the default priming program is preconfigured in the memory.

16. The system of claim 15, wherein the controller is configured to preconfigure the default priming program using priming program parameter values and selection criteria stored in the memory.

17. The system of claims 16, wherein the priming program parameter values comprise electrode selections for spatially defining the default priming field.

18. The system of claim 13, wherein the neuromodulation device comprises an implantable neuromodulation device.

19. The system of claim 18, wherein the controller is further configured to adapt the custom priming program for energy efficiency in response to a result of execution of the testing program.

20. The system of claim 18, further comprising an external device configured to communicate with the implantable neuromodulation device, and wherein the external device is configured to adapt the custom priming program in response to a result of execution of the testing program.

* * * * *